United States Patent [19]

Vignali et al.

[11] Patent Number: 5,332,816

[45] Date of Patent: Jul. 26, 1994

[54] PIPERAZINE-PIPERIDINE COMPOUNDS FOR USE AS STABILIZERS FOR ORGANIC MATERIALS

[75] Inventors: Graziano Vignali; Valerio Borzatta, both of Bologna, Italy

[73] Assignee: Ciba-Geigy Corporation, Ardsley, N.Y.

[21] Appl. No.: 555,283

[22] Filed: Jul. 19, 1990

[30] Foreign Application Priority Data

Jul. 28, 1989 [IT] Italy .................. 21380 A/89

[51] Int. Cl.$^5$ .................. C07D 401/04; C07D 401/14
[52] U.S. Cl. .................. 544/360; 540/575; 544/113; 544/114; 544/198; 544/209; 544/212; 544/213; 544/219; 544/357; 544/364; 544/383; 544/386; 544/389; 544/398; 544/402
[58] Field of Search .................. 540/575; 544/198, 209, 544/212, 213, 219, 357, 360, 364, 383, 386, 389, 398, 402, 113, 114

[56] References Cited

U.S. PATENT DOCUMENTS

| | | | |
|---|---|---|---|
| 4,315,859 | 2/1982 | Nikles | 544/207 |
| 4,316,025 | 2/1982 | Cantatore et al. | 544/364 |
| 4,528,374 | 7/1985 | Nikles | 546/186 |
| 4,695,599 | 9/1987 | Cantatore | 546/186 |
| 5,030,729 | 7/1991 | Cantatore et al. | 546/191 |
| 5,187,275 | 2/1993 | Borzatta et al. | 544/207 |

FOREIGN PATENT DOCUMENTS

| | | |
|---|---|---|
| 0117229 | 8/1984 | European Pat. Off. . |
| 0410934 | 1/1991 | European Pat. Off. . |
| WO8101706 | 6/1981 | PCT Int'l Appl. . |

OTHER PUBLICATIONS

Derwent 84-214929/35, 1984.
C.A. 102, 7684j (1985).

*Primary Examiner*—Mukund J. Shah
*Assistant Examiner*—Y. N. Gupta
*Attorney, Agent, or Firm*—Luther A. R. Hall

[57] ABSTRACT

The present invention relates to novel piperazine-piperidine compounds of the general formula (I)

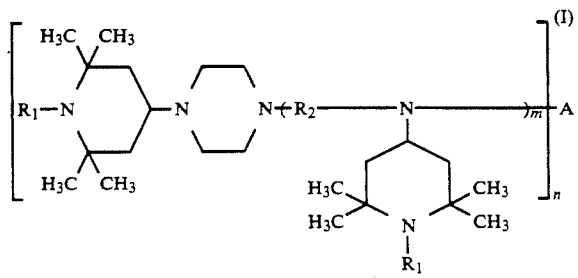

in which $R_1$ is e.g. hydrogen or methyl, $R_2$ is e.g. ethylene, m is zero or 1 and n is e.g. 1, and when n is 1, A is e.g. 2,2-dimethyl-1-propanoyl, n-butoxycarbonyl, n-tetradecyloxycarbonyl or 2,4-bis[N-butyl-(2',2',6',6'-pentamethyl-4'-piperidyl)amino]triazin-6-yl.

The said compounds are effective as light stabilizers, heat stabilizers and oxidation stabilizers for organic materials.

8 Claims, No Drawings

PIPERAZINE-PIPERIDINE COMPOUNDS FOR USE AS STABILIZERS FOR ORGANIC MATERIALS

The present invention relates to novel piperazine-piperidine compounds, to their use as light stabilizers, heat stabilizers and oxidation stabilizers for organic materials, in particular synthetic polymers, and to the organic materials thus stabilized.

It is known that synthetic polymers are subject to photooxidative degradation when they are exposed to sunlight or other sources of ultraviolet light in the presence of oxygen.

For their use in practice, it is therefore necessary to add to them suitable light stabilizers, such as certain benzophenone or benzotriazole derivatives, nickel complexes, substituted benzoic acid esters, alkylidene malonates, cyano acrylates, aromatic oxamides or sterically hindered amines.

Some derivatives of 2,2,6,6-tetramethylpiperidine, for example those described in U.S. Pat. No. 4,316,025 and European Patent 117,229, are effective as light stabilizers.

The present invention relates to novel piperazine-piperidine compounds of the general formula (I)

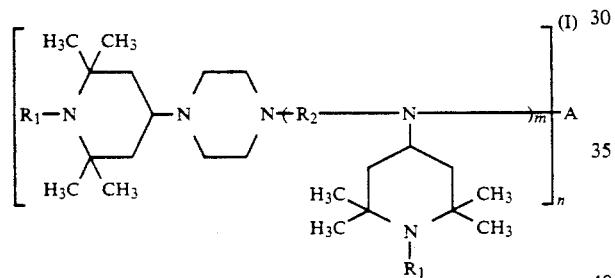

in which $R_1$ is hydrogen, $C_1$–$C_8$alkyl, O•, NO, OH, $CH_2CN$, $C_1$–$C_{18}$alkoxy, $C_5$–$C_{12}$cycloalkoxy, $C_3$–$C_6$alkenyl, $C_7$–$C_9$phenylalkyl which is unsubstituted or mono-, di- or tri-substituted on the phenyl by $C_1$–$C_4$alkyl, $C_1$–$C_8$acyl or $C_2$–$C_4$alkyl substituted by OH in the 2-, 3- or 4-position, $R_2$ is $C_2$–$C_6$alkylene, m is zero or 1, n is 1, 2, 3 or 4 and, if n is 1, A is hydrogen, $C_1$–$C_{18}$alkyl, $C_3$–$C_{18}$alkenyl, $C_7$–$C_9$phenylalkyl which is unsubstituted or mono-, di- or tri-substituted on the phenyl by $C_1$–$C_4$alkyl, or A is one of the groups of the formulae (IIa)–(IId)

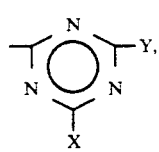 (IIa)

—COR$_3$, (IIb)

—(CO)$_p$COOR$_4$. (IIc)

—SO$_2$R$_5$ (IId)

in which X and Y which can be identical or different are a group —OR$_6$, —SR$_6$ or

where $R_6$, $R_7$ and $R_8$ which can be identical or different are hydrogen, $C_1$–$C_{18}$alkyl, $C_5$–$C_{12}$cycloalkyl which is unsubstituted or mono-, di- or tri-substituted by $C_1$–$C_4$alkyl, $C_3$–$C_{18}$alkenyl, phenyl which is unsubstituted or mono-, di- or tri-substituted by $C_1$–$C_4$alkyl or by $C_1$–$C_4$alkoxy, $C_7$–$C_9$phenylalkyl which is unsubstituted or mono-, di- or tri-substituted on the phenyl by $C_1$–$C_4$alkyl, $C_2$–$C_4$alkyl substituted in the 2-, 3- or 4-position by OH, by $C_1$–$C_8$alkoxy or by di-($C_1$–$C_4$alkyl)-amino, tetrahydrofurfuryl or a group of the formula (III)

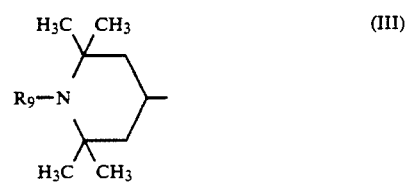

where $R_9$ is as defined for $R_1$, or

is a 5-membered to 7-membered heterocyclic group, $R_3$ is hydrogen, $C_1$–$C_{18}$alkyl, $C_5$–$C_{12}$cycloalkyl which is unsubstituted or mono-, di-or tri-substituted by $C_1$–$C_4$alkyl, $C_2$–$C_{18}$alkenyl, phenyl which is unsubstituted or mono-, di- or tri-substituted by $C_1$–$C_4$alkyl or by $C_1$–$C_4$alkoxy and/or by an OH group, $C_7$–$C_9$phenylalkyl which is unsubstituted or mono-, di- or tri-substituted on the phenyl by $C_1$–$C_4$alkyl and/or by an OH group, p is zero or 1, $R_4$ is $C_1$–$C_{18}$alkyl, $C_5$–$C_{12}$cycloalkyl which is unsubstituted or mono-, di- or tri-substituted by $C_1$–$C_4$alkyl, $C_3$–$C_{18}$alkenyl or a group of the formula (III) and $R_5$ is $C_1$–$C_{18}$alkyl or phenyl which is unsubstituted or mono-, di- or tri-substituted by $C_1$–$C_4$alkyl, and, if n is 2, A is $C_2$–$C_{12}$alkylene, $C_4$–$C_{12}$alkylene interrupted by 1, 2 or 3 oxygen atoms, 2-hydroxytrimethylene, xylylene or one of the groups of the formulae (IVa)–(IVe)

—(CH$_2$)$_q$—CO—, —CO—R$_{10}$—CO—, —COO—R$_{11}$—OOC—,
(IVa) (IVb) (IVc)

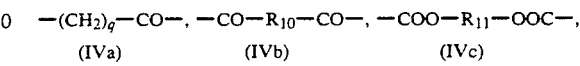
(IVd) (IVe)

in which q is zero or an integer from 1 to 10, $R_{10}$ is a direct bond, $C_1$–$C_{12}$alkylene, cyclohexylene or phenylene, $R_{11}$ is $C_2$–$C_{12}$alkylene, $C_4$–$C_{12}$alkylene interrupted by 1, 2 or 3 oxygen atoms, cyclohexylene, cyclohexylenedimethylene, methylenedicyclohexylene, isopropylidenedicyclohexylene, phenylene, isopropylidenediphenylene or xylylene, Z is as defined above for X and Y or is a group of the formula (V)

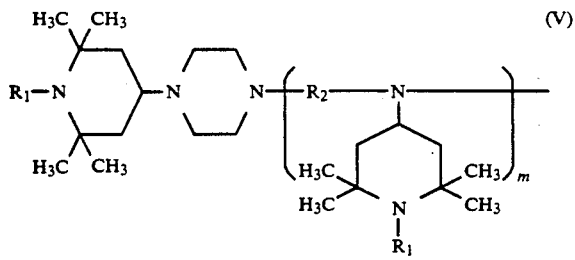
(V)

with $R_1$, $R_2$ and m being as defined above, $D_1$ is one of the groups of the formulae (VIa)–(VIc)

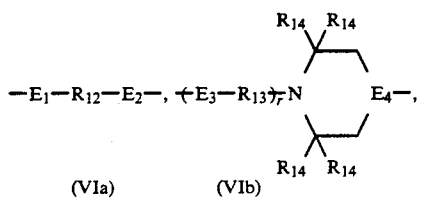

(VIa)    (VIb)

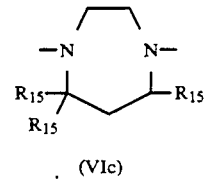

(VIc)

in which $E_1$, $E_2$ and $E_3$ which can be identical or different are —O— or

$R_{12}$ is as defined above for $R_{11}$ or $C_4$–$C_{12}$alkylene interrupted by 1 or 2 groups

$R_{13}$ is $C_2$–$C_6$alkylene, $E_4$ is $>N-(R_{13}-E_3)_s-$, $>CH-O-$ or

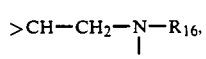

r and s which can be identical or different are zero or 1, $R_{14}$ is hydrogen or also methyl if r is 1 and $E_4$ is $>CH-O-$, $R_{15}$ is hydrogen or methyl and $R_{16}$ is hydrogen, $C_1$–$C_{18}$alkyl, $C_5$–$C_{12}$cycloalky which is unsubstituted or mono-, di- or tri-substituted by $C_1$–$C_4$alkyl, $C_7$–$C_9$phenylalkyl which is unsubstituted or mono-, di- or tri-substituted on the phenyl by $C_1$–$C_4$alkyl, or a group of the formula (III), and, if n is 3, A is aliphatic $C_4$–$C_{18}$triacyl, aliphatic $C_6$–$C_{18}$triacyl containing a trisubstituted nitrogen atom, aromatic $C_9$–$C_{18}$triacyl, heterocyclic triacyl containing up to 18 carbon atoms, or A is a group of the formula (VII)

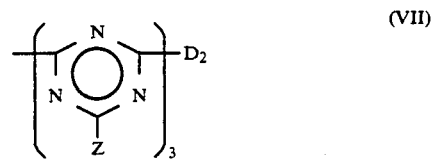
(VII)

in which Z is as defined above and $D_2$ is one of the groups of the formulae (VIIIa)–(VIIId)

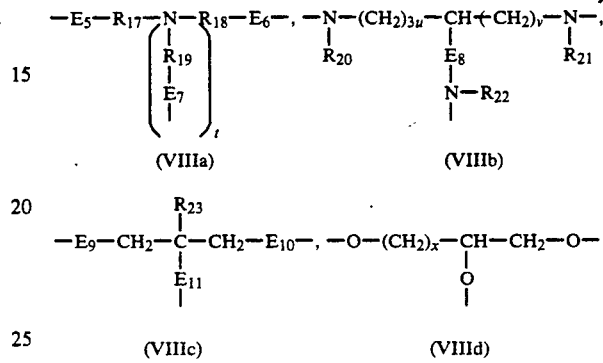

(VIIIa)    (VIIIb)

(VIIIc)    (VIIId)

in which $E_5$, $E_6$, $E_7$, $E_9$, $E_{10}$ and $E_{11}$ which can be identical or different are as defined above for $E_1$, $E_2$ and $E_3$ and, if $E_9$ and $E_{10}$ are —O—, $E_{11}$ is also a —$CH_2$—O— group, $R_{17}$, $R_{18}$ and $R_{19}$ which can be identical or different are $C_2$–$C_6$alkylene, t is zero or 1, $R_{20}$, $R_{21}$ and $R_{22}$ which can be identical or different are as defined above for $R_{16}$, $E_8$ is a direct bond or —$CH_2$—, u, v and x which can be identical or different are integers from 2 to 6 and $R_{23}$ is hydrogen or $C_1$–$C_8$alkyl, and, if n is 4, A is aliphatic $C_6$–$C_{18}$tetraacyl, aliphatic $C_{10}$–$C_{18}$tetraacyl containing 2 trisubstituted nitrogen atoms, aromatic $C_{10}$–$C_{18}$tetraacyl, cycloaliphatic $C_{10}$–$C_{22}$tetraacyl or a group of the formula (IX)

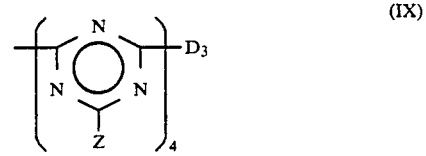
(IX)

in which Z is as defined above and $D_3$ is a group of the formula (Xa) or (Xb)

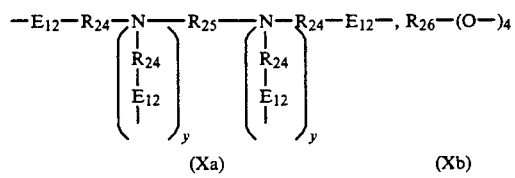

(Xa)    (Xb)

in which $E_{12}$ is as defined above for $E_1$, $E_2$ and $E_3$, $R_{24}$ and $R_{25}$ which can be identical or different are $C_2$–$C_6$alkylene, y is zero or 1 and $R_{26}$ is $C_4$–$C_{12}$alkanetetrayl.

Representative examples of $C_1$–$C_8$alkyl $R_1$, $R_9$ and $R_{23}$ are methyl, ethyl, propyl, butyl, isobutyl, pentyl, hexyl, heptyl and octyl. $C_1$–$C_4$Alkyl is preferred.

Examples of $C_1$–$C_{18}$alkyl are methyl, ethyl, propyl, isopropyl, butyl, 2-butyl, isobutyl, t-butyl, pentyl, 2-pentyl, hexyl, heptyl, octyl, 2-ethylhexyl, t-octyl, nonyl, decyl, undecyl, dodecyl, tridecyl, tetradecyl, hexadecyl and octadecyl.

Examples of $C_2$-$C_4$alkyl substituted by OH are 2-hydroxyethyl, 2-hydroxypropyl, 3-hydroxypropyl, 2-hydroxybutyl and 4-hydroxybutyl. 2-Hydroxyethyl is preferred.

Examples of $C_2$-$C_4$alkyl substituted by $C_1$-$C_8$alkoxy, preferably $C_1$-$C_4$alkoxy, in particular methoxy or ethoxy, are 2-methoxyethyl, 2-ethoxyethyl, 3-methoxypropyl, 3-ethoxypropyl, 3-butoxypropyl, 3-octoxypropyl and 4-methoxybutyl.

Examples of $C_2$-$C_4$alkyl substituted by di-($C_1$-$C_4$alkyl)-amino, preferably by dimethylamino or diethylamino, are 2-dimethylaminoethyl, 2-diethylaminoethyl, 3-dimethylaminopropyl, 3-diethylaminopropyl, 3-dibutylaminopropyl and 4-diethylaminobutyl.

Representative examples of $C_1$-$C_{18}$alkoxy $R_1$ and $R_9$ are methoxy, ethoxy, propoxy, isopropoxy, butoxy, isobutoxy, pentoxy, isopentoxy, hexoxy, heptoxy, octoxy, decyloxy, dodecyloxy, tetradecyloxy, hexadecyloxy and octadecyloxy. $C_6$-$C_{12}$Alkoxy, in particular heptoxy or octoxy, is preferred.

Examples of unsubstituted or substituted $C_5$-$C_{12}$cycloalkyl are cyclopentyl, methylcyclopentyl, dimethylcyclopentyl, cyclohexyl, methylcyclohexyl, dimethylcyclohexyl, trimethylcyclohexyl, t-butylcyclohexyl, cyclooctyl, cyclodecyl and cyclododecyl; unsubstituted or $C_1$-$C_4$alkyl-substituted cyclohexyl is preferred.

Representative examples of $C_5$-$C_{12}$cycloalkoxy $R_1$ and $R_9$ are cyclopentoxy, cyclohexoxy, cycloheptoxy, cyclooctoxy, cyclodecyloxy and cyclododecyloxy. Cyclopentoxy and cyclohexoxy are preferred.

Examples of alkenyl containing up to 18 carbon atoms are vinyl, allyl, 2-methylallyl, hexenyl, decenyl, undecenyl and oleyl.

Examples of substituted phenyl are methylphenyl, dimethylphenyl, trimethylphenyl, t-butylphenyl, di-t-butylphenyl, 3,5-di-t-butyl-4-methylphenyl, methoxyphenyl, ethoxyphenyl, hydroxyphenyl and 3,5-di-t-butyl-4-hydroxyphenyl.

Examples of phenylalkyl which is unsubstituted or substituted on the phenyl are benzyl, methylbenzyl, dimethylbenzyl, trimethylbenzyl, t-butylbenzyl, 2-phenylethyl and 2-(3,5-di-t-butyl-4-hydroxyphenyl)-ethyl.

Representative examples of $C_1$-$C_8$acyl $R_1$ and $R_9$ are formyl, acetyl, propionyl, butyryl, pentanoyl, hexanoyl, heptanoyl, octanoyl, benzoyl, acryloyl and crotonoyl. $C_1$-$C_8$Alkanoyl, $C_3$-$C_8$alkenoyl or benzoyl are preferred. Acetyl is especially preferred.

Representative examples of a 5-membered to 7-membered heterocyclic group $$-N-R_8$$
$$\phantom{-N-}|$$
$$\phantom{-N-}R_7$$

are 1-pyrrolidyl, 1-piperidyl, 4-morpholinyl, 4-methyl-1-piperazinyl, 1-hexahydroazepinyl, 5,5,7-trimethyl-1-homopiperazinyl and 4,5,5,7-tetramethyl-1-homopiperazinyl. 4-Morpholinyl is preferred.

Examples of alkylene containing up to 12 carbon atoms are methylene, ethylene, propylene, trimethylene, tetramethylene, pentamethylene, 2,2-dimethyltrimethylene, hexamethylene, trimethylhexamethylene, decamethylene and dodecamethylene. $R_2$ is preferably ethylene.

Examples of $C_4$-$C_{12}$alkylene interrupted by 1, 2 or 3 oxygen atoms are 3-oxapentane-1,5-diyl, 3,6-dioxaoctane-1,8-diyl, 4,7-dioxadecane-1,10-diyl, 4,9-dioxadodecane-1,12-diyl and 3,6,9-trioxaundecane-1,11-diyl.

Preferred examples of $C_4$-$C_{12}$alkylene $R_{12}$ interrupted by 1 or 2

$$-N-R_{16}$$
$$\phantom{-N-}|$$

groups are 3-azapentane-1,5-diyl, 4-azaheptane-1,7-diyl, 4-methyl-4-azaheptane-1,7-diyl, 4,7-diazadecane-1,10-diyl and 4,7-dimethyl-4,7-diazadecane-1,10-diyl.

Aliphatic $C_4$-$C_{18}$triacyl A can be unsubstituted or substituted by an OH group. Preferred examples are the triacyl derivatives of methanetricarboxylic acid, 1,1,2-ethanetricarboxylic acid, 1,2,3-propanetricarboxylic acid, citric acid and 1,2,3-butanetricarboxylic acid.

Aliphatic $C_6$-$C_{18}$triacyl A substituted by a nitrogen atom is, for example, a group $N[(CH_2)_{1-5}-CO-]_3$, preferably a group $N-(CH_2CO-)_3$.

Aromatic $C_9$-$C_{18}$triacyl A is, for example, a triacyl derivative of 1,2,4-benzenetricarboxylic acid or 1,3,5-benzenetricarboxylic acid.

Heterocyclic triacyl A containing up to 18 carbon atoms is, for example,

Aliphatic $C_6$-$C_{18}$tetraacyl A is, for example, a tetraacyl derivative of 1,1,3,3-propanetetracarboxylic acid or 1,2,3,4-butanetetracarboxylic acid.

Aliphatic $C_{10}$-$C_{18}$tetraacyl A substituted by two nitrogen atoms is, for example, a group of the formula Aromatic $C_{10}$-$C_{18}$tetraacyl A is a tetraacyl derivative of 1,2,4,5-benzenetetracarboxylic acid.

Cycloaliphatic $C_{10}$-$C_{22}$tetraacyl A is, for example, one of the groups

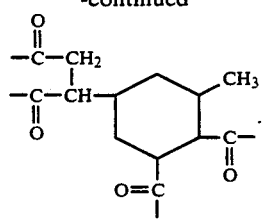

Preferred examples of $C_4$-$C_{12}$alkanetetrayl $R_{26}$ are 1,2,3,4-butanetetrayl and the group

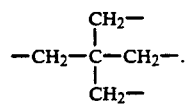

The preferred definitions of $R_1$ and $R_9$ are hydrogen, $C_1$-$C_4$alkyl, OH, $C_6$-$C_{12}$alkoxy, $C_5$-$C_8$cycloalkoxy, allyl, benzyl, acetyl and 2-hydroxyethyl, in particular hydrogen and methyl.

Those compounds of the formula (I) are preferred in which $R_2$ is $C_2$-$C_6$alkylene, m is zero or 1, n is 1, 2, 3 or 4 and, if n is 1, A is hydrogen, $C_1$-$C_{18}$alkyl, $C_3$-$C_6$alkenyl or benzyl or A is one of the groups of the formulae (IIa)–(IId) in which X and Y which can be identical or different are a group —$OR_6$, —$SR_6$ or 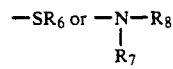

where $R_6$, $R_7$ and $R_8$ which can be identical or different are hydrogen, $C_1$-$C_{18}$alkyl, $C_5$-$C_8$cycloalkyl which is unsubstituted or mono-, di- or tri-substituted by $C_1$-$C_4$alkyl, $C_3$-$C_{18}$alkenyl, phenyl which is unsubstituted or mono-, di- or tri-substituted by $C_1$-$C_4$alkyl or by $C_1$-$C_4$alkoxy, benzyl, $C_2$-$C_3$alkyl substituted in the 2- or 3-position by OH, by $C_1$-$C_4$alkoxy or by di-($C_1$-$C_4$alkyl)-amino, tetrahydrofurfuryl or a group of the formula (III), or the group

is 1-pyrrolidyl, 1-piperidyl, 4-morpholinyl or 1-hexahydroazepinyl, $R_3$ is hydrogen, $C_1$-$C_{17}$alkyl, $C_5$-$C_8$cycloalkyl which is unsubstituted or mono-, di- or tri-substituted by $C_1$-$C_4$alkyl, $C_2$-$C_{17}$alkenyl, phenyl which is unsubstituted or mono-, di- or tri-substituted by $C_1$-$C_4$alkyl and/or by an OH group, $C_7$-$C_8$phenylalkyl which is unsubstituted or mono-, di- or tri-substituted on the phenyl by $C_1$-$C_4$alkyl and/or by an OH group, p is zero or 1, $R_4$ is $C_1$-$C_{18}$alkyl, $C_5$-$C_8$cycloalkyl which is unsubstituted or mono-, di- or tri-substituted by $C_1$-$C_4$alkyl, $C_3$-$C_{18}$alkenyl or a group of the formula (III) and $R_5$ is $C_1$-$C_{12}$alkyl, phenyl or tolyl, and, if n is 2, A is $C_2$-$C_{10}$alkylene, $C_4$-$C_{10}$alkylene interrupted by 1, 2 or 3 oxygen atoms, 2-hydroxytrimethylene, xylylene or one of the groups of the formulae (IVa)–(IVe) in which q is an integer from 1 to 5, $R_{10}$ is a direct bond, $C_1$-$C_{10}$alkylene or cyclohexylene, $R_{11}$ is $C_2$-$C_{10}$ alkylene, $C_4$-$C_{10}$alkylene interrupted by 1, 2 or 3 oxygen atoms, cyclohexylenedimethylene, isopropylidenedicyclohexylene or isopropylidenediphenylene, Z is as defined above for X and Y or a group of the formula (V), $D_1$ is one of the groups of the formulae (VIa)–(VIc) in which $E_1$, $E_2$ and $E_3$ which can be identical or different are —O— or

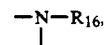

$R_{12}$ is as defined above for $R_{11}$, methylenedicyclohexylene or $C_4$-$C_{12}$alkylene interrupted by 1 or 2 groups

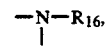

$R_{13}$ is $C_2$-$C_6$alkylene, $E_4$ is

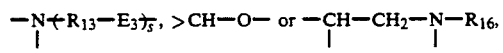

r and s which can be identical or different are zero or 1, $R_{14}$ is hydrogen or also methyl if r is 1 and $E_4$ is >CH—O—, $R_{15}$ is hydrogen or methyl and $R_{16}$ is hydrogen, $C_1$-$C_{12}$alkyl, $C_5$-$C_8$cycloalkyl which is unsubstituted or mono-, di- or tri-substituted by $C_1$-$C_4$alkyl, benzyl or a group of the formula (III), and, if n is 3, A is aliphatic $C_4$-$C_{12}$triacyl, a group N—($CH_2$—CO—)$_3$, aromatic or heterocyclic triacyl containing up to 12 carbon atoms or A is a group of the formula (VII) in which Z is as defined above and $D_2$ is one of the groups of the formulae (VIIIa)–(VIIId) in which $E_5$, $E_6$, $E_7$, $E_9$, $E_{10}$ and $E_{11}$ which can be identical or different are as defined above for $E_1$, $E_2$ and $E_3$ and, if $E_9$ and $E_{10}$ are —O—, $E_{11}$ is also a —$CH_2$—O— group, $R_{17}$, $R_{18}$ and $R_{19}$ which can be identical or different are $C_2$-$C_6$alkylene, t is zero or 1, $R_{20}$, $R_{21}$ and $R_{22}$ which can be identical or different are as defined above for $R_{16}$, $E_8$ is a direct bond or —$CH_2$—, u, v and x which can be identical or different are integers from 2 to 6 and $R_{23}$ is hydrogen or $C_1$-$C_4$alkyl, and, if n is 4, A is aliphatic $C_6$-$C_8$tetraacyl, aliphatic $C_{10}$-$C_{14}$tetraacyl containing two trisubstituted nitrogen atoms or a group of the formula (IX) in which Z is as defined above and $D_3$ is a group of the formula (Xa) or (Xb) in which $E_{12}$ is as defined above for $E_1$, $E_2$ and $E_3$, $R_{24}$ and $R_{25}$ which can be identical or different are $C_2$-$C_6$alkylene, y is zero or 1 and $R_{26}$ is $C_4$-$C_8$alkanetetrayl.

Those compounds of the formula (I) are particularly preferred in which $R_2$ is $C_2$-$C_3$alkylene, m is zero or 1, n is 1, 2, 3 or 4 and, if n is 1, A is hydrogen, $C_1$-$C_{18}$alkyl, allyl, benzyl or A is one of the groups of the formulae (IIa)–(IId) in which X and Y which can be identical or different are a group —$OR_6$, —$SR_6$ or

where $R_6$, $R_7$ and $R_8$ which can be identical or different are hydrogen, $C_1$-$C_{12}$alkyl, cyclohexyl which is unsubstituted or mono-, di- or tri-substituted by $C_1$-$C_4$alkyl, allyl, undecenyl, oleyl, phenyl, benzyl, $C_2$-$C_3$alkyl substituted in the 2- or 3-position by OH, by $C_1$-$C_4$alkoxy, by dimethylamino or by diethylamino, tetrahydrofurfuryl or a group of the formula (III), or the group

is 4-morpholinyl, $R_3$ is $C_1$–$C_{17}$alkyl, cyclohexyl which is unsubstituted or mono-, di- or tri-substituted by $C_1$–$C_4$alkyl, $C_2$–$C_{10}$alkenyl, phenyl, t-butylphenyl, 3,5-di-t-butyl-4-hydroxyphenyl, benzyl or 2-(3,5-di-t-butyl-4-hydroxyphenyl)-ethyl, p is zero or 1, $R_4$ is $C_1$–$C_{18}$alkyl, cyclohexyl which is unsubstituted or mono-, di- or tri-substituted by $C_1$–$C_4$alkyl, allyl, undecenyl, oleyl or a group of the formula (III) and $R_5$ is $C_1$–$C_8$alkyl, phenyl or tolyl and, if n is 2, A is $C_2$–$C_8$alkylene, $C_4$–$C_8$alkylene interrupted by 1 or 2 oxygen atoms, 2-hydroxytrimethylene, xylylene or one of the groups of the formulae (IVa)–(IVe) in which q is an integer from 1 to 3, $R_{10}$ is a direct bond or $C_1$–$C_8$alkylene, $R_{11}$ is $C_2$–$C_8$alkylene, $C_4$–$C_8$alkylene interrupted by 1 or 2 oxygen atoms, cyclohexylenedimethylene, isopropylidenedicyclohexylene or isopropylidenediphenylene, Z is as defined above for X and Y or is a group of the formula (V), $D_1$ is one of the groups of the formulae (VIa)–(VIc) in which $E_1$, $E_2$ and $E_3$ which can be identical or different are —O— or

$R_{12}$ is as defined above for $R_{11}$, methylenedicyclohexylene or $C_4$–$C_{10}$alkylene interrupted by 1 or 2 groups

$R_{13}$ is $C_2$–$C_3$alkylene, $E_4$ is

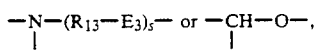

r and s which can be identical or different are zero or 1, $R_{14}$ is hydrogen or also methyl if r is 1 and $E_4$ is >CH—O—, $R_{15}$ is hydrogen or methyl and $R_{16}$ is hydrogen, $C_1$–$C_8$alkyl, cyclohexyl which is unsubstituted or mono-, di- or tri-substituted by $C_1$–$C_4$alkyl, benzyl or a group of the formula (III), and, if n is 3, A is aliphatic $C_4$–$C_8$triacyl, 1,2,4-benzenetricarbonyl, 1,3,5-benzenetricarbonyl or A is a group of the formula (VII) in which Z is as defined above and $D_2$ is one of the groups of the formulae (VIIIa)–(VIIId) in which $E_5$, $E_6$, $E_7$, $E_9$, $E_{10}$ and $E_{11}$ which can be identical or different are as defined above for $E_1$, $E_2$ and $E_3$ and, if $E_9$ and $E_{10}$ are —O—, $E_{11}$ is also a group —$CH_2$—O—, $R_{17}$, $R_{18}$ and $R_{19}$ which can be identical or different are $C_2$–$C_6$alkylene, t is zero or 1, $R_{20}$, $R_{21}$ and $R_{22}$ which can be identical or different are as defined above for $R_{16}$, $E_8$ is a direct bond or —$CH_2$—, u, v and x which can be identical or different are integers from 2 to 6, $R_{23}$ is hydrogen, methyl or ethyl, and, if n is 4, A is aliphatic $C_6$–$C_8$tetraacyl or a group of the formula (IX) in which Z is as defined above and $D_3$ is a group of the formula (Xa) or (Xb) in which $E_{12}$ is as defined above for $E_1$, $E_2$ and $E_3$, $R_{24}$ and $R_{25}$ which can be identical or different are $C_2$–$C_6$alkylene, y is zero or 1 and $R_{26}$ is $C_4$–$C_6$alkanetetrayl.

Those compounds of the formula (I) are of special interest in which $R_2$ is $C_2$–$C_3$alkylene, m is zero or 1, n is 1, 2, 3 or 4 and, if n is 1, A is hydrogen, methyl, $C_4$–$C_{18}$alkyl or A is one of the groups of the formulae (IIa)–(IIc) in which X and Y which can be identical or different are a group —$OR_6$ or

where $R_6$ is $C_1$–$C_8$alkyl, 2,2,6,6-tetramethyl-4-piperidyl or 1,2,2,6,6-pentamethyl-4-piperidyl, $R_7$ and $R_8$ which can be identical or different are $C_1$–$C_{12}$alkyl, cyclohexyl, benzyl, $C_2$–$C_3$alkyl substituted in the 2- or 3-position by methoxy, by ethoxy, by dimethylamino or by diethylamino, tetrahydrofurfuryl, 2,2,6,6-tetramethyl-4-piperidyl or 1,2,2,6,6-pentamethyl-4-piperidyl or $R_7$ is also hydrogen or the group

is 4-morpholinyl, $R_3$ is $C_3$–$C_{17}$alkyl, cyclohexyl, phenyl, 3,5-di-t-butyl-4-hydroxyphenyl or 2-(3,5-di-t-butyl-4-hydroxyphenyl)-ethyl, p is zero, $R_4$ is $C_2$–$C_{18}$alkyl, cyclohexyl, trimethylcyclohexyl, t-butylcyclohexyl, 2,2,6,6-tetramethyl-4-piperidyl or 1,2,2,6,6-pentamethyl-4-piperidyl and, if n is 2, A is one of the groups of the formulae (IVa)–(IVe) in which q is 1, $R_{10}$ is a direct bond or $C_1$–$C_8$alkylene, $R_{11}$ is $C_2$–$C_8$alkylene, cyclohexylenedimethylene or isopropylidenedicyclohexylene, Z is as defined above for X and Y or is a group of the formula (V), $D_1$ is one of the groups of the formulae (VIa)–(VIc) in which $E_1$ and $E_2$ which can be identical or different are —O— or

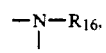

$R_{12}$ is $C_2$–$C_8$alkylene, cyclohexylenedimethylene or methylenedicyclohexylene, the group (VIb) is

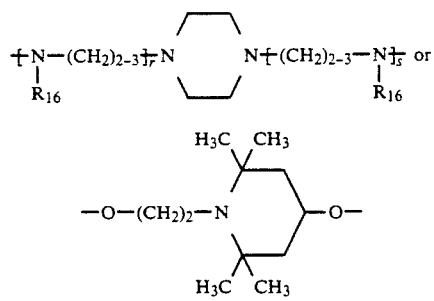

where r and s which can be identical or different are zero or 1, $R_{16}$ is hydrogen, $C_1$–$C_4$alkyl, cyclohexyl, 2,2,6,6-tetramethyl-4-piperidyl or 1,2,2,6,6-pentamethyl-4-piperidyl and $R_{15}$ is hydrogen or methyl, and, if n is 3, A is a group of the formula (VII) in which Z is as defined above and $D_2$ is a group of the formula (VIIIa) or (VIIIb) in which $E_5$, $E_6$ and $E_7$ which can be identical or different are as defined above for $E_1$ and $E_2$, $R_{17}$ and $R_{18}$ which can be identical or different are $C_2$–$C_6$alkylene, t is zero, $R_{20}$, $R_{21}$ and $R_{22}$ are as defined above for $R_{16}$, $E_8$ is a direct bond or —$CH_2$— and u and v which can be identical or different are integers from 2 to 6, and, if n is 4, A is a group of the formula (IX) in which Z is as defined above and $D_3$ is a group of the formula (Xa) in which $E_{12}$ is as defined above for $E_1$ and $E_2$, $R_{24}$ and $R_{25}$ which can be identical or different are $C_2$-$C_3$alkylene and y is zero.

Those compounds of the formula (I) are of particular interest in which $R_1$ is hydrogen or methyl, $R_2$ is ethylene, m is zero or 1, n is 1, 2, 3 or 4 and, if n is 1, A is hydrogen, methyl, $C_8$-$C_{18}$alkyl or A is one of the groups of the formulae (IIa)-(IIc) in which X and Y which can be identical or different are a group —$OR_6$ or

where $R_6$ is $C_1$-$C_4$alkyl, 2,2,6,6-tetramethyl-4-piperidyl or 1,2,2,6,6-pentamethyl-4-piperidyl, $R_7$ and $R_8$ which can be identical or different are $C_1$-$C_8$alkyl, cyclohexyl, tetrahydrofurfuryl, 2,2,6,6-tetramethyl-4-piperidyl or 1,2,2,6,6-pentamethyl-4-piperidyl, or $R_7$ is also hydrogen, or the group

is 4-morpholinyl, $R_3$ is $C_4$-$C_{17}$alkyl, p is zero and $R_4$ is $C_2$-$C_{18}$alkyl, cyclohexyl, t-butylcyclohexyl, 2,2,6,6-tetramethyl-4-piperidyl or 1,2,2,6,6-pentamethyl-4-piperidyl, and, if n is 2, A is one of the groups of the formulae (IVb)-(IVe) in which $R_{10}$ is $C_2$-$C_8$-alkylene, $R_{11}$ is $C_4$-$C_6$alkylene, Z is as defined above for X and Y or a group of the formula (V), $D_1$ is 1,4-piperazinediyl or a group of the formula (VIa) in which $E_1$ and $E_2$ are

$R_{12}$ is $C_2$-$C_6$alkylene or methylenedicyclohexylene, $R_{16}$ is hydrogen, methyl, 2,2,6,6-tetramethyl-4-piperidyl or 1,2,2,6,6-pentamethyl-4-piperidyl, and, if n is 3, A is a group of the formula (VII) in which Z is as defined above and $D_2$ is a group

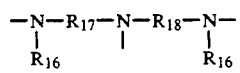

in which $R_{16}$ is as defined above and $R_{17}$ and $R_{18}$ are $C_2$-$C_3$alkylene, and, if n is 4, A is a group of the formula (IX) in which Z is as defined above and $D_3$ is a group

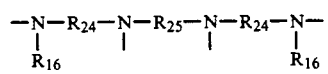

in which $R_{16}$ is as defined above and $R_{24}$ and $R_{25}$ which can be identical or different are $C_2$-$C_3$alkylene.

Those compounds of the formula (I) are also of particular interest in which $R_1$ is hydrogen or methyl, $R_2$ is ethylene, m is zero or 1, n is 1, 2 or 3 and, if n is 1, A is hydrogen, methyl, $C_8$-$C_{18}$alkyl or A is one of the groups of the formulae (IIa)-(IIc) in which X and Y which can be identical or different are

where $R_7$ and $R_8$ which can be identical or different are $C_1$-$C_8$alkyl, 2,2,6,6-tetramethyl-4-piperidyl or 1,2,2,6,6-pentamethyl-4-piperidyl, or $R_7$ is also hydrogen, or the group

is 4-morpholinyl, $R_3$ is $C_4$-$C_{17}$alkyl, p is zero and $R_4$ is $C_2$-$C_{18}$alkyl, and, if n is 2, A is one of the groups of the formulae (IVb)-(IVe) in which $R_{10}$ is $C_2$-$C_8$alkylene, $R_{11}$ is $C_4$-$C_6$alkylene, Z is as defined above for X and Y or a group of the formula (V), $D_1$ is 1,4-piperazindiyl or a group of the formula (VIa) in which $E_1$ and $E_2$ are

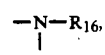

$R_{12}$ is $C_2$-$C_6$alkylene, $R_{16}$ is 2,2,6,6-tetramethyl-4-piperidyl or 1,2,2,6,6-pentamethyl-4-piperidyl, and, if n is 3, A is a group of the formula (VII) in which Z is as defined above and $D_2$ is a group

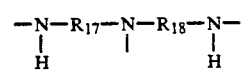

in which $R_{17}$ and $R_{18}$ are $C_2$-$C_3$alkylene.

The compounds of the formula (I) can be prepared according to processes known per se, e.g. by reacting a compound of the formula (XI)

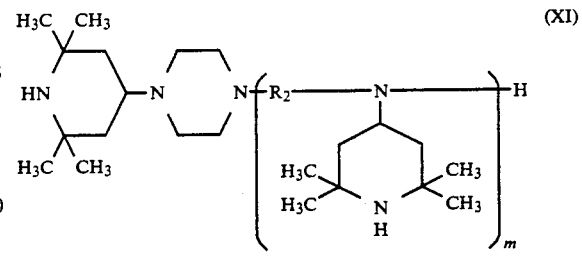

with $R_2$ and m being as defined above, with suitable alkylating or acylating reagents in the appropriate molar ratios. In this way, the compounds of the formula (I) with $R_1$=H are obtained, from which the corresponding compounds with $R_1 \neq H$ can subsequently be obtained.

The reactions are conveniently carded out in an inert solvent, working at temperatures from e.g. $-20°$ C. to $200°$ C., preferably from $-10°$ C. to $180°$ C.

The compounds of the formula (XI) can be prepared, for example, according to Scheme 1 or Scheme 2, i.e. by reacting a compound of the formula (XII) or (XIII) with 2,2,6,6-tetramethyl-4-piperidone to give an enamine of the formula (XIV) or an enamine-ketimine of the formula (XV), which are then hydrogenated in the presence of a hydrogenation catalyst such as e.g. platinum, palladium or nickel.

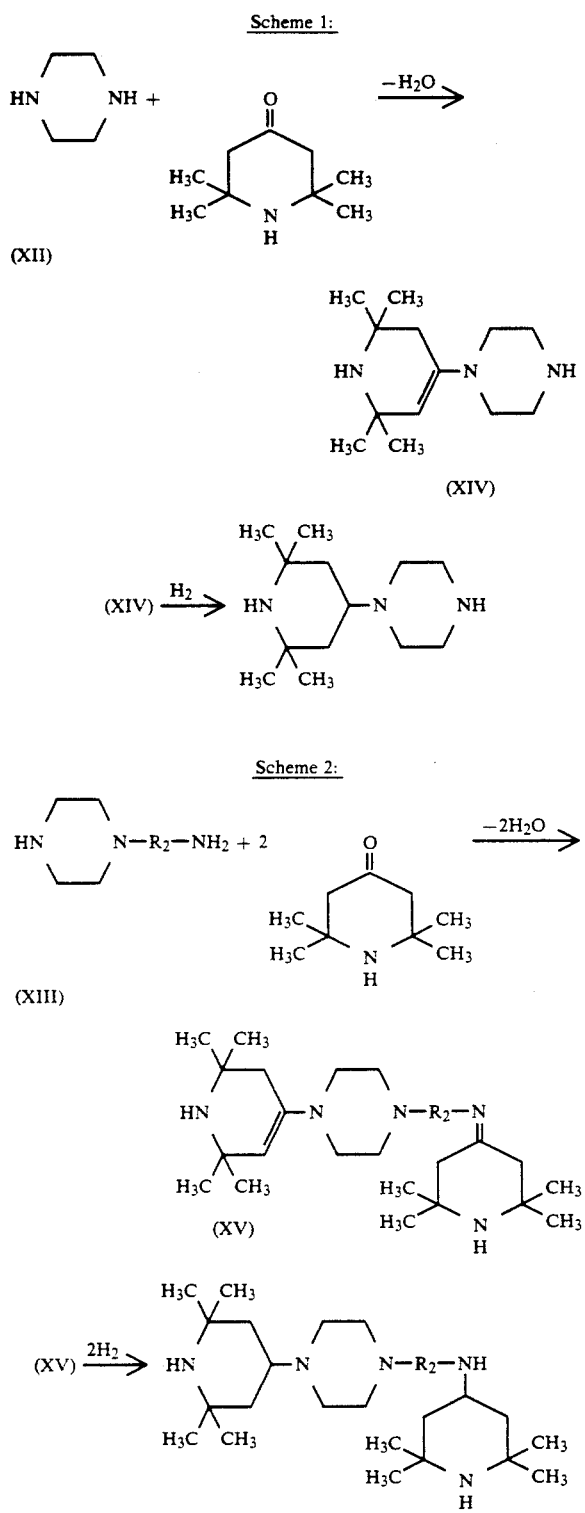

The reactions according to Scheme 1 or 2 are preferably carried out in the same reactor, working without solvent or in the presence of an aliphatic or aromatic hydrocarbon solvent having a boiling point between e.g. 60° C. and 180° C., preferably between 80° C. and 140° C.; the hydrogenation can also be carried out in the presence of a $C_1$–$C_4$ alcohol.

The compounds of the formula (XI) can also be prepared directly by catalytic hydrogenation of a mixture of a compound of the formula (XII) or (XIII) with 2,2,6,6-tetramethyl-4-piperidone, without a solvent or in a $C_1$–$C_4$ alcohol, preferably in the presence of an organic or inorganic acid such as benzoic acid or sulfuric acid, in a quantity of e.g. 0.001 to 0.05 mole per mole of 2,2,6,6-tetramethyl-4-piperidone.

As mentioned at the outset, the compounds of the formula (I) are highly effective in improving the light stability, heat stability and oxidation stability of organic materials, in particular synthetic polymers and copolymers.

Examples of such organic materials which can be stabilized are:

1. Polymers of monoolefins and diolefins, for example polypropylene, polyisobutylene, polybutene-1, polymethylpentene-1, polyisoprene or polybutadiene, as well as polymers of cycloolefins, for instance of cyclopentene or norbornene, polyethylene (which optionally can be crosslinked), for example high-density polyethylene (HDPE), low-density polyethylene (LDPE) and linear low-density polyethylene (LLDPE).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, such as, for example, ethylene/propylene, linear low-density polyethylene (LLDPE) and its mixtures with low-density polyethylene (LDPE), propylene/butene-1, ethylene/hexene, ethylene/ethylpentene, ethylene/heptene, ethylene/octene, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidenenorbornene; as well as mixtures of such copolymers and their mixtures with polymers mentioned in 1) above, for example polypropylene/ethylene-propylene copolymers, LDPE/EVA, LDPE/EAA, LLDPE/EVA and LLDPE/EAA.

3a. Statistical or alternating copolymers of α-olefines with carbon monoxide.

3b. Hydrocarbon resins (for example $C_5$–$C_9$) and hydrogenated modifications thereof (for example tackifiers).

4. Polystyrene, poly-(p-methylstyrene), poly-(α-methylstyrene).

5. Copolymers of styrene or α-methylstyrene with dienes or acrylic derivatives, such as, for example, styrene/acrylonitrile, styrene/alkyl methacrylate, styrene/maleic anhydride, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer/and block copolymers of styrene, such as, for example, styrene/butadiene/styrene, styrene/isoprene/styrene, styrene/ethylene/butylene/styrene or styrene/ethylene/propylene/styrene.

6. Graft copolymers of styrene or α-methylstyrene such as, for example, styrene on polybutadiene, styrene on polybutadiene-styrene or polybutadiene-acrylonitrile; styrene and acrylonitrile (or methacrylonitrile) on polybutadiene; styrene and maleic anhydride or maleimide on polybutadiene; styrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the mixtures known as ABS, MBS, ASA or AES polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example polyvinyl chloride, polyvinylidene chloride, polyvinyl fluoride, polyvinylidene fluoride, as well as copolymers thereof, as for example vinyl chloride/vinylidene chloride, vinyl chloride/vinyl acetate or vinylidene chloride/vinyl acetate copolymers.

8. Polymers which are derived from α,β-unsaturated acids and derivatives thereof, such as polyacrylates and polymethacrylates, polyacrylamide and polyacrylonitrile.

9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinyl butyral, polyallyl phthalate or polyallylmelamine; as well as their copolymers with olefins mentioned in 1) above.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and polyoxymethylenes which contain ethylene oxide as a comonomer; polyacetals modified with thermoplastic polyurethanes, acrylates or MBS.

13. Polyphenylene oxides and sulfides, and mixtures of polyphenylene oxides with polystyrene or polyamides.

14. Polyurethanes which are derived from polyethers, polyesters or polybutadienes with terminal hydroxyl groups on the one hand and on the other hand aliphatic or aromatic polyisocyanates, as well as precursors thereof (polyisocyanates, polyols or prepolymers).

15. Polyamides and copolyamides which are derived from aliamines and dicarboxylic acids and/or from aminocarboxylic acids or the corresponding lactams, such as polyamide 4, polyamide 6/6, polyamide 6/10, 6/9, 6/12 and 4/6, polyamide 11, polyamide 12, aromatic polyamides obtained by condensation of m-xylenediamine and adipic acid; polyamides prepared from hexamethylenediamine and isophthalic and/or terephthalic acid and optionally an elastomer as modifier, for example poly-2,4,4-trimethyl-hexamethylene-terephthalamide or poly-m-phenylene-isophthalamide. Further, copolymers of the aforementioned polyamides with polyolefins, olefin copolymers, ionomers or chemically bonded or grafted elastomers; or with polyethers, such as, for instance, with polyethylene glycols, polypropylene glycols or polytetramethylene glycols. Polyamides or copolyamides modified with EPDM or ABS. Polyamides condensed during processing (RIM-polyamide systems).

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylolcyclohexane terephthalate, poly-[2,2-(4-hydroxyphenyl)-propane] terephthalate and polyhydroxybenzoate as well as block copolyether-esters derived from polyethers having hydroxyl end groups.

18. Polycarbonates and polyester-carbonates.

19. Polysulfones, polyether-sulfones and polyether-ketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low inflammability.

23. Thermosetting acrylic resins, derived from substituted acrylic esters, such as epoxy-acrylates, urethane-acrylates or polyester-acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatine and derivatives thereof which are chemically modified in a polymer-homologous manner, such as cellulose acetates, cellulose propionates and cellulose butyrates, or cellulose ethers, such as methylcellulose; rosins and their derivatives.

27. Mixtures of polymers as mentioned above, for example PP/EPDM, polyamide 6/EPDM or ABS, PVC/EVA, PVC/ABS, PVC/MBS, PC/ASA, PC/PBT, PVC/CPE, PVC/acrylates, POM/thermoplastic PUR, PC/thermoplastic PUR, POM/acrylate, POM/MBS, PPE/HIPS, PPE/PA 6/6 and copolymers, PA/HDPE, PA/PP, PA/PPE.

28. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.

29. Aqueous emulsions of natural or synthetic rubbers, for example natural latex or latexes of carboxylated styrene/butadiene copolymers.

The compounds of the formula (I) are particularly suitable for improving the light stability, heat stability and oxidation stability of polyolefins, especially polyethylene and polypropylene. The compounds of the formula (I) can be used in mixtures with organic materials in various proportions depending on the nature of the material to be stabilized, on the end use and on the presence of other additives.

In general, it is appropriate to use, for example, 0.01 to 5% by weight of the compounds of the formula (I), relative to the weight of the material to be stabilized, preferably from 0.05 to 1%.

The compounds of the formula (I) can be incorporated in the polymeric materials by various processes, such as dry mixing in the form of powder, or wet mixing in the form of solutions or suspensions or also in the form of a masterbatch; in such operations, the polymer can be used in the form of powder, granules, solutions, suspensions or in the form of latices.

In general, the compounds of the formula (I) can be added to the polymeric materials before, during or after the polymerization or cross-linking of said materials.

The materials stabilized with the products of the formula (I) can be used for the production of mouldings, films, tapes, monofilaments, fibres, surface coatings and the like.

If desired, other conventional additives for synthetic polymers, such as antioxidants, UV absorbers, nickel stabilizers, pigments, fillers, plasticizers, antistatic agents, flameproofing agents, lubricants, corrosion inhibitors and metal deactivators, can be added to the mixtures of the compounds of the formula (I) with the organic materials.

Particular examples of additives which can be used in a mixture with the compounds of the formula (I) are:

1. Antioxidants
   1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenyl, 2,6-di-tert-butyl-4-methoxymethylphenol, 2,6-dinonyl-4-methylphenol.
   1.2. Alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol.
   1.3. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol).
   1.4. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethlylidenebis(6-tert-butyl-4-isobutylphenol), 2,2'-methlylenebis[6-(α-methylbenzyl)-4-nonylphenol], 2,2'-methlylenebis[6-(αα-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methylphenyl)-dicyclopentadiene, bis[2-(3'-tert-butyl-2'-hydroxy-5'-methylbenzyl)-6-tert-butyl-4-methylphenyl] terephthalate.
   1.5. Benzyl compounds, for example 1,3,5-tris(3,5-di-tert-butyl-4-hydroxybenzyl)-2,4,6-trimethyl benzene, bis(3,5-di-tert-butyl-4-hydroxybenzyl) sulfide, isooctyl 3,5-di-tert-butyl-4-hydroxybenzylmercapto-acetate, bis(4-tert-butyl-3-hydroxy-2,6-dimethylbenzyl) dithiolterephthalate, 1,3,5-tris(3,5-di-tert-butyl-4-hydroxybenzyl) isocyanurate, 1,3,5-tris(4-tert-butyl-3-hydroxy-2,6-dimethylbenzyl) isocyanurate, dioctadecyl 3,5-di-tert-butyl-4-hydroxybenzylphosphonate, calcium salt of monoethyl, 3,5-di-tert-butyl-4-hydroxybenzylphosphonate, 1,3,5-tris(3,5-dicyclohexyl-4-hydroxybenzyl) isocyanurate.
   1.6. Acylaminophenols, for example lauric acid 4-hydroxyanilide, stearic acid 4-hydroxyanilide, 2,4-bis(octylmercapto)-6-(3,5-di-tert-butyl-4-hydroxyanilino)-s-triazine, octyl N-(3,5-di-tert-butyl-4-hydroxyphenyl)-carbamate.
   1.7. Esters of β-(3,5-di-tert-butyl-4-hydroxyphenyl)-propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalic acid diamide.
   1.8. Esters of β-(5-ter-butyl-4-hydroxy-3-methylphenyl)propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'bis(hydroxyethyl)oxalic acid diamide.
   1.9. Esters of β-(3,5-dicyclohexyl-4-hydroxyphenyl)-propionicacid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalic acid diamide.
   1.10. Amides of β-(3,5-di-tert-butyl-4-hydroxyphenyl)propionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl)trimethylenediamine, N,N'-bis(3,5-di-tert-butyl-4-hydroxyphenylpropionyl)hydrazine.
2. UV absorbers and light stabilizers
   2.1. 2-(2'-Hydroxyphenyl)benzotriazoles, for example the 5'-methyl, 3',5'-di-tert-butyl, 5'-tert-butyl, 5'-(1,1,3,3-tetramethylbutyl), 5-chloro-3',5'-di-tert-butyl, 5-chloro-3'-tert-butyl-5'-methyl, 3'-sec-butyl-5'-tert-butyl, 4'-octoxy-3',5'-di-tert-amyl and 3',5'-bis(α,α-dimethylbenzyl) derivatives.
   2.2. 2-Hydroxybenzophenones, for example the 4-hydroxy, 4-methoxy, 4-octoxy, 4-decyloxy, 4- dodecyloxy, 4-benzyloxy, 4,2',4'-trihydroxy and 2'-hydroxy-4,4'-dimethoxy derivatives.

2.3. Esters of substituted and unsubstituted benzoic acids, for example 4-tert-butylphenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate and hexadecyl 3,5-di-tert-butyl-4-hydroxybenzoate.

2.4. Acrylates, for example ethyl $\alpha$-cyano-$\beta,\beta$-diphenylacrylate, isooctyl $\alpha$-cyano-$\beta,\beta$-diphenylacrylate, methyl $\alpha$-carbomethoxycinnamate, methyl $\alpha$-cyano-$\beta$-methyl-p-methoxycinnamate, butyl $\alpha$-cyano-$\beta$-methyl-p-methoxycinnamate, methyl $\alpha$-carbomethoxy-p-methoxycinnamate and N-($\beta$-carbomethoxy-$\beta$-cyanovinyl)-2-methylindoline.

2.5. Nickel compounds, for example nickel complexes of 2,2'-thiobis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of 4-hydroxy-3,5-di-tert-butylbenzylphosphonic acid monoalkyl esters, e.g. of the methyl or ethyl ester, nickel complexes of ketoximes, e.g. of 2-hydroxy-4-methylphenyl undecyl ketoxime, nickel complexes of 1-phenyl-4-1-lauroyl-5-hydroxypyrazole, with or without additional ligands.

2.6. Sterically hindered amines, for example bis(2,2,6,6-tetramethylpiperidyl) sebacate, bis(1,2,2,6,6-pentamethylpiperidyl) sebacate, bis-(1,2,2,6,6-pentamethylpiperidyl) n-butyl-3,5-di-tert-butyl-4-hydroxybenzylmalonate, the condensation product of 1-hydroxyethyl-2,2,6,6-tetramethyl-4-hydroxypiperidine and succinic acid, the condensation product of N,N'-bis(2,2,6,6-tertramethyl-4-piperidyl)hexamethylenediamine and 4-tert-octylamino-2,6-dichloro-1,3,5-trazine, tris(2,2,6,6-tetramethyl-4-piperidyl) nitrilotriacetate, tetrakis(2,2,6,6-tetramethyl-4-piperidyl), 1,2,3,4-butanetetracarboxylate, 1,1'-(1,2-ethanediyl)bis-(3,3,5,5-tetramethylpiperazinone).

2.7. Oxalic acid diamides, for example, 4,4'-dioctyloxyoxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylaminopropyl)oxalamide, 2-ethoxy-5-tert-butyl-2'-ethyloxanilide and its mixtures with 2-ethoxy-2'-ethyl-5,4'-di-tert-butyloxanilide and mixtures of ortho- and paramethoxy-disubstituted oxanilides and mixtures of o- and p-ethoxy-disubstituted oxanilides.

2.8 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine.

3. Metal deactivators, for example N,N'-diphenyloxalic acid diamide, N-salicylal-N'-salicyloylhydrazine, N,N'-bis(salicyloyl)hydrazine, N,N'-bis(3,5-di-tert-butyl-4-hydroxyphenylpropionyl 1)hydrazine, 3-salicyloylamino-1,2,4-triazole, bis(benzylidene)oxalodihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, tristearyl sorbitol triphosphite, tetrakis(2,4-di-tert-butylphenyl) 4,4'-biphenylenediphosphonite, 3,9-bis(2,4-di-tert-butylphenoxy)-2,4,8,10-tetraoxa-3,9-dipho sphaspiro[5.5]undecane.

5. Peroxide scavengers, for example esters of $\beta$-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis($\beta$-dodecylmercapto)propionate.

6. Polyamide stabilizers, for example copper salts in combination with iodides and/or phosphorus compounds and salts of divalent manganese.

7. Basic co-stabilizers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example Ca stearate, Zn stearate, Mg stearate, Na ricinoleate and K palmirate, antimony pyrocatecholate or zinc pyrocatecholate.

8. Nucleating agents, for example 4-tert-butyl-benzoic acid, adipic acid, diphenylacetic acid.

9. Fillers and reinforcing agents, for example calcium carbonate, silicates, glass fibres, asbestos, talc, kaolin, mica, barium sulfate, metal oxides and hydroxides, carbon black, graphite.

10. Other additives, for example plasticizers, lubricants, emulsifiers, pigments, optical brighteners, flameproofing agents, antistatic agents and blowing agents.

The compounds of the invention can also be used as stabilizers, especially as light stabilizers, for almost all materials known in the an of photographic reproduction and other reproduction techniques as e.g. described in Research Disclosure 1990, 31429 (pages 474 to 480).

In order to illustrate the present invention more clearly, several examples of the preparation of compounds of the formula (I) are described below; these examples are given by way of illustration only and do not imply any restriction. The compounds disclosed in Examples 3, 10, 11, 16 and 17 correspond to a particular preferred embodiment of the present invention.

EXAMPLE 1

Preparation of N,4-bis-(2,2,6,6-tetramethyl-4-piperidyl)-1-piperazine-ethaneamine.

155.2 g (1 mol) of 2,2,6,6-tetramethyl-4-piperidone, 64.5 g (0.5 mol) of 1-piperazine-ethaneamine and 250 ml of toluene are heated under reflux with removal of the water of reaction.

The solvent is then removed in vacuo and the residue thus obtained is diluted with 250 ml of methanol and hydrogenated at 95° C. in the presence of 5 g of 5% Pt-on-carbon at a hydrogen pressure of 50 bar until absorption ceases (about 10 hours).

After cooling to ambient temperature, the catalyst is removed by filtration and the product is separated off by distillation; boiling point 171° C./0.07 mbar.

Analysis for C₂₄H₄₉N₅ Calculated: C=70.73%; H=12.11%; N=14.17% Found: C=70.16%; H=12.18%; N=17.14%

EXAMPLE 2

Preparation of 1-(2,2,6,6-tetramethyl-4-piperidyl)-piperazine.

155.2 g (1 mol) of 2,2,6,6-tetramethyl-4-piperidone, 137.82 g (1.6 mol) of piperazine and 250 ml of toluene are heated under reflux with removal of the water of reaction.

The solvent is removed in vacuo and the residue thus obtained is diluted with 250 ml of methanol and hydrogenated at 80° C. in the presence of 5 g of 5% Pt-on-carbon at a hydrogen pressure of 50 bar until absorption ceases (about 10 hours).

After cooling to ambient temperature, the catalyst is removed by filtration and volatile components are removed by distillation under reduced pressure. The residue is treated with warm acetone; this gives a product of melting point 125°-126° C.

Analysis for C₁₃H₂₇N₃ Calculated: C=69.28%; H=12.08%; N=18.64% Found: C=68.66%; H=12.01%; N=18.45%

EXAMPLE 3

Preparation of the compound of the formula

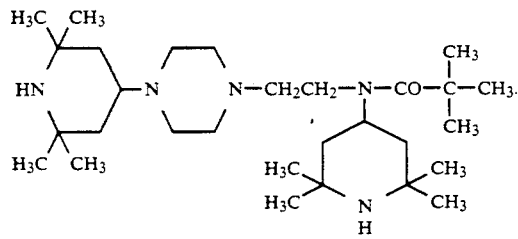

A solution of 6.03 g (0.05 mol) of pivaloyl chloride in 30 ml of dichloromethane is added slowly to a solution, cooled to −5° C., of 20.35 g (0.05 mol) of the product from Example 1 in 200 ml of dichloromethane. During the addition, the temperature is maintained at about 0° C. The solution is stirred for 2 hours at ambient temperature and then cooled to 0° C. A solution of 2.37 g (0.06 mol) of sodium hydroxide in 15 ml of water is then added slowly, maintaining the temperature at 0°-5° C. After one hour at this temperature, the organic phase is separated off, washed with water, dried over Na₂SO₄ and evaporated. Crystallization of the residue from acetone gives a product of melting point 117°-120° C.

Analysis for C₂₉H₃₇N₅O Calculated: C=70.83%; H=11.68%; N=14.24% Found: C=70.64%; H=11.70%; N=14.32%

EXAMPLES 4-13

Following the procedure described in Example 3 and using the product from Example 1 or Example 2 with the appropriate reagents, the following compounds of the formula

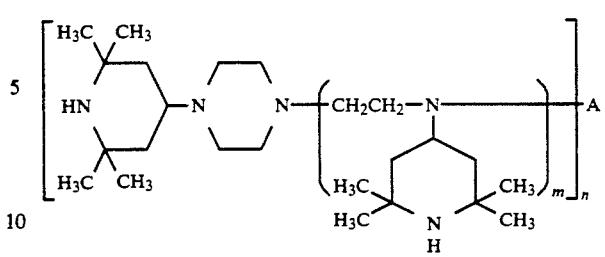

are prepared.

| Example | m | n | A | m.p. (°C.) |
|---|---|---|---|---|
| 4 | 0 | 1 | —COOC₁₈H₃₇ | 48–49 |
| 5 | 0 | 2 | —CO—(CH₂)₈—OC— | 123–124 |
| 6 | 0 | 2 | —CO—(CH₂)₂—OC— | 177–178 |
| 7 | 0 | 2 | —COO—(CH₂)₆—OOC— | 92–94 |
| 8 | 0 | 2 | —CO—(CH₂)₄—OC— | 157–158 |
| 9 | 0 | 2 | —COO—(CH₂)₄—OOC— | 162–163 |
| 10 | 1 | 1 | —COOC₄H₉ | oil |
| 11 | 1 | 1 | —COOC₁₄H₂₉ | oil |
| 12 | 1 | 2 | —COO—(CH₂)₄—OOC— | 146–148 |
| 13 | 1 | 2 | —CO—(CH₂)₂—OC— | 177–180 |

EXAMPLE 14

Preparation of the compound of the formula

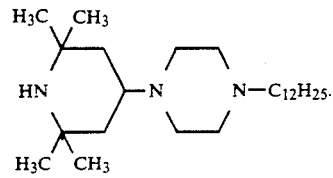

11.25 g (0.05 mol) of the product from Example 2, 12.45 g (0.05 mol) of 1-bromododecane, 6.91 g (0.05 mol) of potassium carbonate and 0.63 g (0.004 mol) of potassium iodide in 50 ml of ethanol are heated under reflux for 6 hours. After cooling to ambient temperature and filtering off the salts, the solvent is removed in vacuo and the residue thus obtained is dissolved in 50 ml of dichloromethane. The solution is washed several times with water, dried over Na₂SO₄ and evaporated. Crystallization of the residue from acetone gives a product of melting point 25°-28° C.

Analysis for C₂₅H₅₁N₃ Calculated: C=76.27%; H=13.06%; N=10.67% Found: C=75.94%; H=13.04%; N=10.38%

EXAMPLE 15

Preparation of the compound of the formula

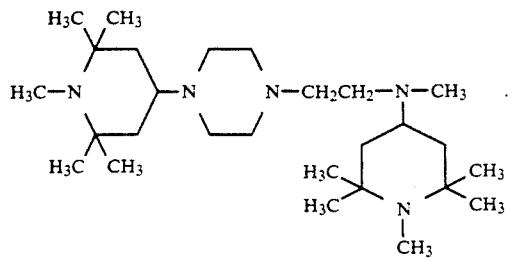

61.15 g (0.15 mol) of the product from Example 1 are dissolved at ambient temperature in a solution of 69 g (1.5 mol) of formic acid in 120 ml of water. 22.5 g (0.9 mol) of paraformaldehyde are added to the solution obtained, and the mixture is heated under reflux for 8 hours. After cooling to ambient temperature, a solution of 60 g (1.5 mol) of sodium hydroxide in 200 ml of water is added; an oil separates out, which is then extracted with dichloromethane. The organic phase is then separated off, washed several times with water and dried over $Na_2SO_4$.

Evaporation of the solvent gives a solid of melting point 67°–70° C.

Analysis for $C_{27}H_{55}N_5$ Calculated: C=72.08%; H=12.33%; N=15.56% Found: C=71.65%; H=12.37%; N=15.62%

EXAMPLE 16

Following a procedure analogous to that described in Example 15 and using 45.29 g (0.07 mol) of the product from Example 11, 12.6 g (0.42 mol) of paraformaldehyde and 48.3 g (1.05 mol) of formic acid, an oily compound of the formula

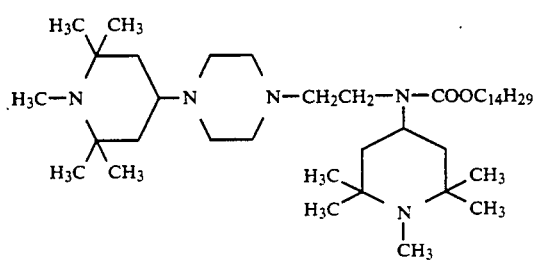

is obtained.

Analysis for $C_{41}H_{81}N_5O_2$ Calculated: C=72.80%; H=12.07%; N=10.36% Found: C=73.10%; H=12.20%; N=10.33%

EXAMPLE 17

Preparation of the compound of the formula

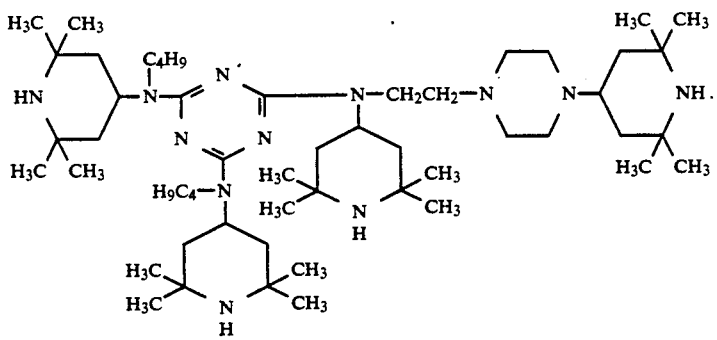

26.77 g (0.05 mol) of 2-chloro-4,6-bis-[N-(2,2,6,6-tetramethyl-4-piperidyl)butylamino]-1,3,5-triazine, 20.35 g (0.05 mol) of the product from Example 1 and 4.0 g (0.1 mol) of sodium hydroxide in 120 ml of xylene are heated under reflux for 18 hours, with azeotropic removal of the water of reaction. The mixture is cooled to about 50° C. and filtered, and the filtrate is washed with water. The solution is then dried over sodium sulfate and evaporated in vacuo.

The residue is crystallized from acetone.

This gives a product of melting point 186°–188° C.

Analysis for $C_{53}H_{102}N_{12}$ Calculated: C=70.15%; H=11.33%; N=18.52% Found: C=69.88%; H=11.32%; N=18.42%

EXAMPLE 18

Preparation of the compound of the formula

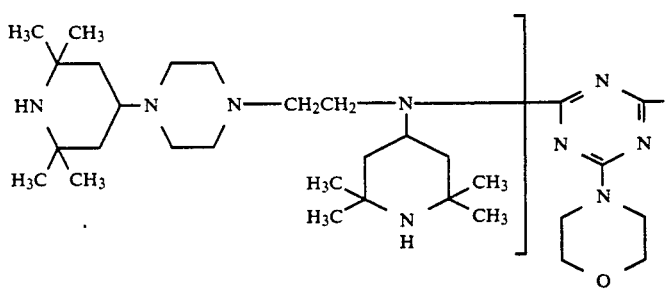

11.75 g (0.05 mol) of 2,4-dichloro-6-morpholino-1,3,5-triazine, 40.7 g (0.1 mol) of the product from Example 1 and 120 ml of xylene are heated for 2 hours at 90° C. 8 g (0.2 mol) of sodium hydroxide are added and the mixture is heated under reflux for 18 hours, with removal of the water of reaction. The mixture is cooled to about 50° C., filtered, washed with water, dried over $Na_2SO_4$ and evaporated in vacuo. The residue is crystallized from acetone. The product obtained has a melting point of 181°–183° C.

Analysis for $C_{55}H_{104}N_{14}O$ Calculated: C=67.58%; H=10.72%; N=20.06% Found: C=66.90%; H=10.65%; N=19.90%

EXAMPLE 19

Preparation of the compound of the formula

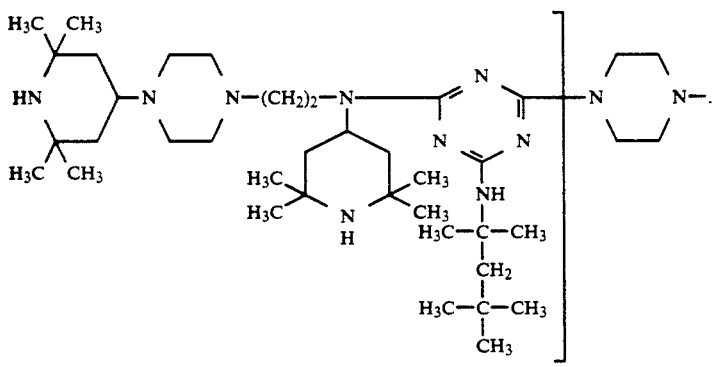

A solution of 15.79 g (0.06 mol) of N-(4,6-dichloro-1,3,5-triazin-2-yl)-t-octylamine in 100 ml of xylene is added slowly to a solution of 24.42 g (0.06 mol) of the product from Example 1 in 40 ml of xylene, maintained at 0° C. After the end of the addition, the mixture is heated for 2 hours at 60° C. and then cooled to ambient temperature, and a solution of 2.4 g (0.03 mol) of sodium hydroxide in 10 ml of water is added. The mixture is heated for 2 hours at 60° C. and cooled, the phases separating. 2.6 g (0.06 mol) of piperazine are then added to the organic solution, and the mixture is heated under reflux for 4 hours. After cooling, a solution of 2.8 g (0.07 mol) of sodium hydroxide in 20 ml of water is added. The mixture is stirred for a further 2 hours, the phases are separated, and the organic phase is washed several times with water and dried over $Na_2SO_4$, and the residue, after evaporation of the solvent, is crystallized from acetone, giving a solid of melting point 153°–156° C.

Analysis for $C_{74}H_{140}N_{20}$ Calculated: C=67.85%; H=10.77%; N=21.38% Found: C=67.22%; H=10.78%; N=20.79%

EXAMPLE 20

Preparation of the compound of the formula

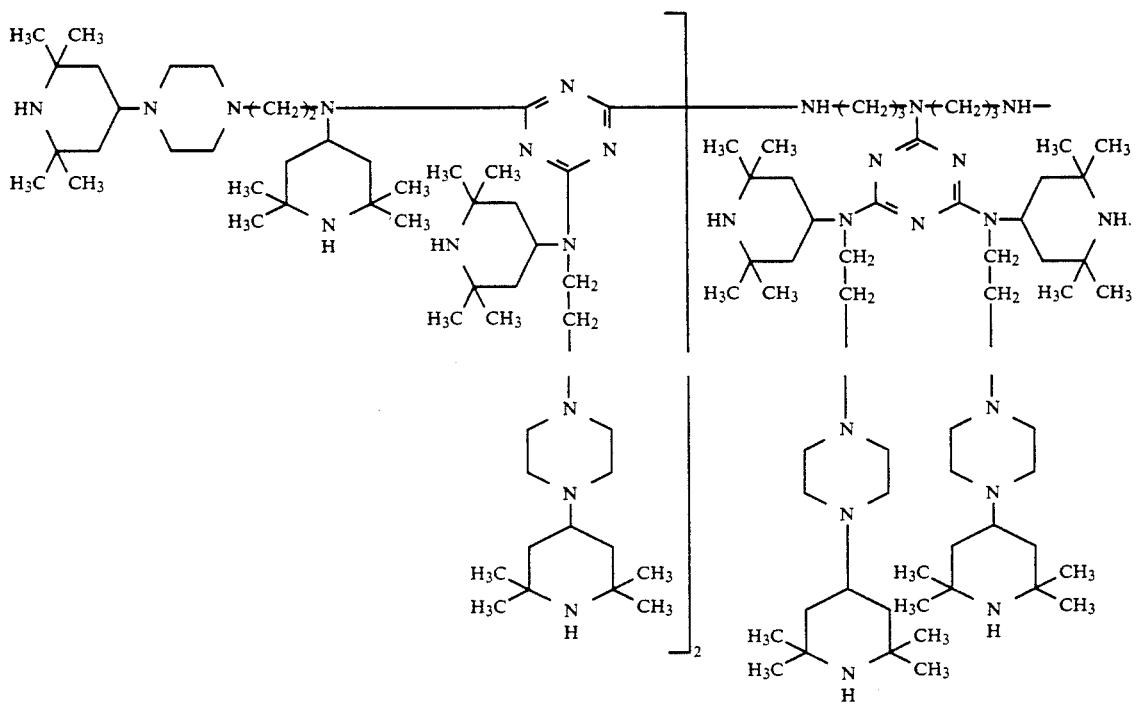

A) Preparation of N,N',N''-tris-(4,6-dichloro-1,3,5-triazin-2-yl)-N-3-aminopropyl-propanediamine.

A solution of 6.56 g (0.05 mol) of N-3-aminopropyl-propanediamine in 50 ml of dichloromethane is added to a mixture, cooled to −5° C., containing 27.68 g (0.15 mol) of cyanuric chloride in 200 ml of dichloromethane and 6.3 g (0.16 mol) of sodium hydroxide in 15 ml of water. During the addition, the temperature is maintained at −5° C. The mixture is then stirred for 4 hours at ambient temperature. A precipitate forms which is filtered off and washed with dichloromethane.

This gives a white solid of melting point 219°–222° C.

B) 8.63 g (0.015 mol) of N,N',N''-tris-(4,6-dichloro-1,3,5-triazin-2-yl)-N-3-aminopropyl-propanediamine, 36.62 g (0.09 mol) of the product from Example 1 and 100 ml of trimethylbenzene are heated for 4 hours at 80° C. 18.66 g (0.135 mol) of potassium carbonate are then added, and the mixture is heated under reflux for 18 hours with removal of the water of reaction. The mixture is cooled, filtered, washed with water and dried over Na$_2$SO$_4$. After evaporation of the solvent, this gives a product of melting point 168°-171° C.

Analysis for C$_{159}$H$_{302}$N$_{42}$ Calculated: C=68.15%; H=10.86%; N=20.99% Found: C=67.53%; H=10.76%; N=20.75%

EXAMPLE 21

Preparation of the compound of the formula

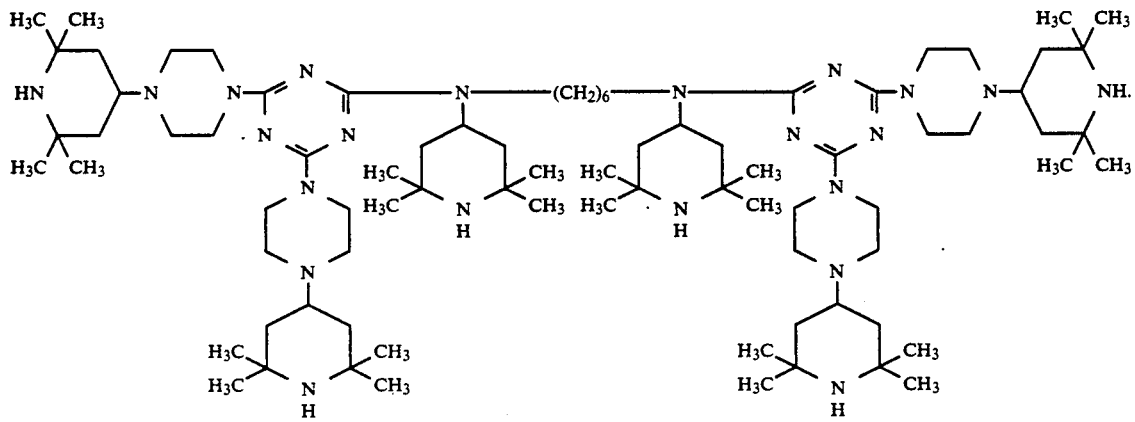

A) Preparation of N,N'-bis(4,6-dichloro-1,3,5-triazin-2-yl)-N,N'-bis(2,2,6,6-tetramethyl-4-piperidyl)-1,6-diaminohexane.

A solution of 11.82 g (0.03 mol) of N,N'-bis(2,2,6,6-tetramethyl-4-piperidyl)-1,6-diaminohexane in 50 ml of 1,2-dichloroethane is added slowly in the course of 2 hours to a solution, maintained at 0° C., containing 11.07 g (0.06 mol) of cyanuric chloride in 100 ml of 1,2-dichloroethane.

50 ml of an aqueous solution containing 2.52 g (0.063 mol) of sodium hydroxide are then added in 30 minutes at 0° C., and stirring is continued for 2 hours at 0° C. The aqueous phase is then separated off, the organic phase is washed repeatedly with water and dried over anhydrous sodium sulfate, and a white solid of melting point 161°-163° C. is precipitated by evaporation of the solvent.

B) A mixture containing 10.35 g (0.015 mol) of N,N'-bis(4,6-dichloro-1,3,5-triazin-2-yl)-N,N'-bis(2,2,6,6-tetramethyl-4-piperidyl)-1,6-diaminohexane, 13.5 g (0.06 mol) of the product from example 2, 100 ml of xylene and 2.4 g (0.06 mol) of sodium hydroxide dissolved in 10 ml of water is heated for 5 hours at 100° C.

After cooling a precipitate forms which is filtered off and dissolved in dichloromethane. The solution is then washed with water, dried over Na$_2$SO$_4$ and the solvent is evaporated. A solid of melting point 157°-159° C. is obtained.

Analysis for C$_{82}$H$_{152}$N$_{22}$ Calculated: C=68.08%; H=10.59%; N=21.31% Found: C=67.61%; H=10.54%; N=21.27%

EXAMPLE 22

Light-stabilizing action in polypropylene tapes.

1 g of each of the compounds indicated in Table 1, 1.0 g of tris-(2,4-di-t-butylphenyl)phosphite, 0.5 g of pentaerythritol tetrakis-3-(3,5-di-t-butyl-4-hydroxyphenyl)-propionate and 1 g of calcium stearate are mixed in a slow mixer with 1000 g of polypropylene powder of melt index=2 g/10 minutes (measured at 230° C. and 2.16 kg).

The mixtures are extruded at 200°-230° C. to give polymer granules which are then converted into stretched tapes of 50 μm thickness and 2.5 mm widths, using a pilot-type apparatus (®Leonard-Sumirago (VA) Italy) and operating under the following conditions:

| Extruder temperature | 210-230° C. |
|---|---|
| Head temperature | 240-260° C. |
| Stretch ratio | 1:6 |

The tapes thus prepared are exposed, mounted on a white card, in a Weather-O-Meter 65 WR (ASTM G26-77) with a black panel temperature of 63° C. The residual tenacity is measured on samples, taken after various times of exposure to light, by means of a constant-speed tensometer; the exposure time (in hours) needed to halve the initial tenacity (T$_{50}$) is then calculated. Tapes prepared under the same conditions as indicated above, but without addition of stabilizer, are exposed for comparison.

The results obtained are shown in Table 1.

TABLE 1

| Stabilizer | T$_{50}$ (hours) |
|---|---|
| Without stabilizer | 500 |
| Compound from Example 3 | 3400 |
| Compound from Example 6 | 2340 |
| Compound from Example 7 | 2670 |
| Compound from Example 8 | 2560 |
| Compound from Example 9 | 2830 |
| Compound from Example 10 | 3320 |
| Compound from Example 11 | 2610 |
| Compound from Example 12 | 2770 |
| Compound from Example 13 | 2590 |
| Compound from Example 16 | 2650 |
| Compound from Example 17 | 2340 |
| Compound from Example 18 | 2520 |

EXAMPLE 23

Light-stabilizing action in polypropylene plaques.

1 g of each of the compounds indicated in Table 2, 1.0 g of tris-(2,4-di-t-butylphenyl)phosphite, 0.5 g of pentaerythritol tetrakis-3-(3,5-di-t-butyl-4-hydroxyphenyl)-propionate, 1 g of phthalocyanine blue, 1 g of calcium stearate and 1000 g of polypropylene powder of melt index=2 g/10 minutes (measured at 230° C. and 2.16 kg) are intimately mixed in a slow mixer.

The mixtures obtained are extruded at a temperature of 200°-230° C. to give polymer granules which are then convened into plaques of 2 mm thickness by injection-moulding at 190°-220° C.

The plaques obtained are exposed in a model 65 WR Weather-O-Meter (ASTM G26-77) with a black panel temperature of 63° C. until superficial embrittlement (chalking) starts.

A polypropylene plate prepared under the same conditions as indicated above, but without addition of the compounds of the invention, is exposed for comparison.

The exposure time (in hours) needed to reach the start of superficial embrittlement is shown in Table 2.

TABLE 2

| Stabilizer | Time to embrittlement (hours) |
| --- | --- |
| Without stabilizer | 550 |
| Compound from Example 3 | 4000 |
| Compound from Example 10 | 4200 |
| Compound from Example 11 | 4700 |
| Compound from Example 16 | 4350 |

EXAMPLE 24

Anti-oxidant action in polypropylene plaques.

1 g of each of the compounds indicated in Table 3 and 1 g of calcium stearate are mixed in a slow mixer with 1000 g of polypropylene powder of melt index=2 g/10 minutes (measured at 230° C. and 2.16 kg).

The mixtures are extruded twice at 200°-220° C. to give polymer granules which are then convened into plaques of 1 mm thickness by compression-moulding at 230° C. for 6 minutes.

The plaques are then punched using a DIN 5345 1 mould, and the specimens obtained are exposed in a forced-circulation air oven maintained at a temperature of 135° C.

The specimens are checked at regular intervals by folding them by 180° in order to determine the time (in hours) required for fracturing them.

The results obtained are given in Table 3.

TABLE 3

| Stabilizer | Time to fracture (in hours) |
| --- | --- |
| Without stabilizer | 250 |
| Compound from Example 17 | 1350 |
| Compound from Example 18 | 1140 |

EXAMPLE 25

Light stabilizing action in polypropylene fibres.

2.5 g of each of the products indicated in Table 4, 1.0 g of tris-(2,4-di-tert-butyl-phenyl)phosphite, 0.5 g of calcium monoethyl 3,5-di-tert-butyl-4-hydroxybenzyl-phosphonate, 1 g of calcium stearate and 2.5 g of titanium dioxide are mixed in a slow mixer with 1000 g of polypropylene powder of melt index=12 g/10 minutes (measured at 230° C. and 2.16 kg).

The mixtures are extruded at 200°-230° C. to give polymer granules which are then converted into fibres, using a pilot-type apparatus (®Leonard, Sumirago (VA) Italy) and operating under the following conditions.

| | |
| --- | --- |
| Extruder temperature | 200-230° C. |
| Head temperature | 255-260° C. |
| Stretch ratio | 1:3.5 |
| Count | 11 dtex per filament |

The fibres thus prepared are exposed, mounted on white card, in a model 65 WR Weather-O-Meter (ASTM G 26-77) with a black panel temperature of 63° C.

The residual tenacity is measured on samples, taken after various times of exposure to light, by means of a constant-speed tensometer, and the exposure time (in hours) needed to halve the initial tenacity ($T_{50}$) is then calculated.

Fibres prepared under the same conditions as indicated above but without addition of the compounds of the invention, are exposed for comparison.

The results obtained are shown in Table 4:

| Stabilizer | $T_{50}$ (hours) |
| --- | --- |
| None | 150 |
| Compound from Example 20 | 1850 |
| Compound from Example 21 | 1420 |

What is claimed is:

1. A compound of the formula (I)

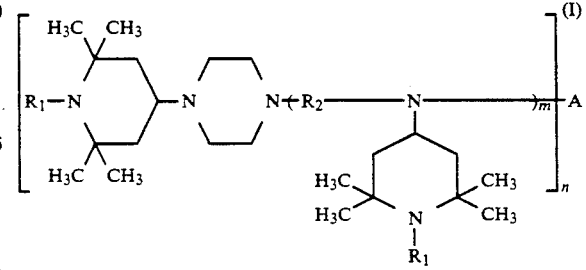

in which $R_1$ is hydrogen, $C_1$-$C_8$alkyl, O•, NO, OH, $CH_2CN$, $C_1$-$C_{18}$alkoxy, $C_5$-$C_{12}$cycloalkoxy, $C_3$-$C_6$alkenyl, $C_714$ $C_9$phenylalkyl which is unsubstituted or mono-, di-or tri-substituted on the phenyl by $C_1$-$C_4$alkyl, $C_1$-$C_8$acyl or $C_2$-$C_4$alkyl substituted by OH in the 2-, 3- or 4-position, $R_2$ is $C_2$-$C_6$alkylene, m is zero or 1, n is 1, 2, 3 or 4 and, if n is 1, A is hydrogen, $C_1$-$C_{18}$alkyl, $C_3$-$C_{18}$alkenyl, $C_7$-$C_9$phenylalkyl which is unsubstituted or mono-, di- or tri-substituted on the phenyl by $C_1$-$C_4$alkyl, or A is one of the groups of the formulae (IIa)–(IId)

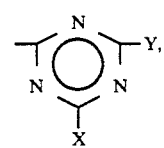

—$COR_3$,   (IIb)

$-(CO)_p̄COR_4$,   (IIc)

—$SO_2R_5$   (IId)

in which X and Y which can be identical or different are a group —$OR_6$, —$SR_6$ or

where $R_6$, $R_7$ and $R_8$ which can be identical or different are hydrogen, $C_1$-$C_{18}$alkyl, $C_5$-$C_{12}$cycloalkyl which is unsubstituted or mono-, di- or tri-substituted by $C_1$-$C_4$alkyl, $C_3$-$C_{18}$alkenyl, phenyl which is unsubstituted or mono-, di- or tri-substituted by $C_1$-$C_4$alkyl or by $C_1$-$C_4$alkoxy, $C_7$-$C_9$phenylalkyl which is unsubstituted or mono-, di- or tri-substituted on the phenyl by $C_1$-$C_4$alkyl, $C_2$-$C_4$alkyl substituted in the 2-, 3- or 4-position by OH, by $C_1$-$C_8$alkoxy or by di-($C_1$-$C_4$alkyl)-amino, tetrahydrofurfuryl or a group of the formula (III)

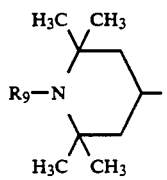

(III)

where $R_9$ is as defined for $R_1$, or

is a 5-membered to 7-membered heterocyclic group, $R_3$ is hydrogen, $C_1$-$C_{18}$alkyl, $C_5$-$C_{12}$cycloalkyl which is unsubstituted or mono-, di-or tri-substituted by $C_1$-$C_4$alkyl, $C_2$-$C_{18}$alkenyl, phenyl which is unsubstituted or mono-, di- or tri-substituted by $C_1$-$C_4$alkyl or by $C_1$-$C_4$alkoxy and/or by an OH group, $C_7$-$C_9$phenylalkyl which is unsubstituted or mono-, di- or tri-substituted on the phenyl by $C_1$-$C_4$alkyl and/or by an OH group, p is zero or 1, $R_4$ is $C_1$-$C_{18}$alkyl, $C_5$-$C_{12}$cycloalkyl which is unsubstituted or mono-, di- or tri-substituted by $C_1$-$C_4$alkyl, $C_3$-$C_{18}$alkenyl or a group of the formula (III) and $R_5$ is $C_1$-$C_{18}$alkyl or phenyl which is unsubstituted or mono-, di- or tri-substituted by $C_1$-$C_4$alkyl, and, if n is 2, A is $C_2$-$C_{12}$alkylene, $C_4$-$C_{12}$alkylene interrupted by 1, 2 or 3 oxygen atoms, 2-hydroxytrimethylene, xylylene or one of the groups of the formulae (IVa)–(IVe)

$-(CH_2)_q-CO-$, (IVa)

$-CO-R_{10}-CO-$, (IVb)

$-COO-R_{11}-OOC-$, (IVc)

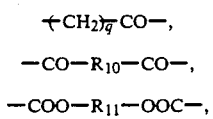

(IVd)

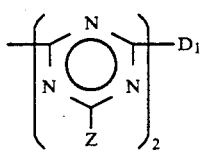

(IVe)

in which q is zero or an integer from 1 to 10, $R_{10}$ is a direct bond, $C_1$-$C_{12}$alkylene, cyclohexylene or phenylene, $R_{11}$ is $C_2$-$C_{12}$alkylene, $C_4$-$C_{12}$alkylene interrupted by 1, 2 or 3 oxygen atoms, cyclohexylene, cyclohexylenedimethylene, methylenedicyclohexylene, isopropylidenedicyclohexylene, phenylene, isopropylidenediphenylene or xylylene, Z is as defined above for X and Y or is a group of the formula (V)

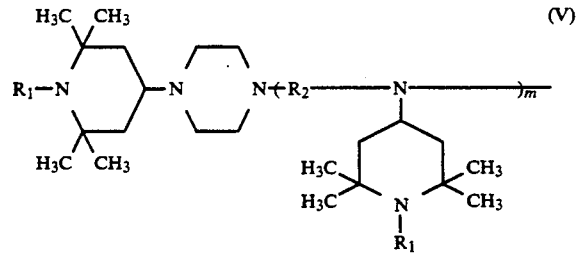

(V)

with $R_1$, $R_2$ and m being as defined above, $D_1$ is one of the groups of the formulae (VIa)–(VIc)

$-E_1-R_{12}-E_2-$, (VIa)

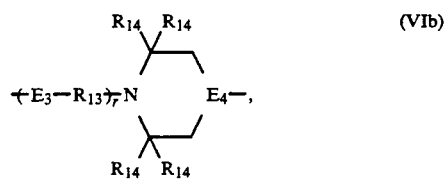

(VIb)

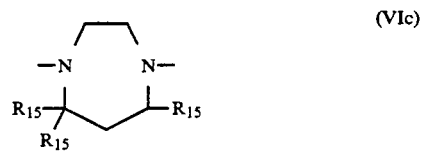

(VIc)

in which $E_1$, $E_2$ and $E_3$ which can be identical or different are $-O-$ or

$R_{12}$ is as defined above for $R_{11}$ or $C_4$-$C_{12}$alkylene interrupted by 1 or 2 groups

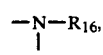

$R_{13}$ is $C_2$-$C_6$alkylene, $E_4$ is $>N-(R_{13}-E_3)_s-$, $>CH-O-$ or

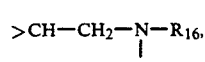

r and s which can be identical or different are zero or 1, $R_{14}$ is hydrogen or also methyl if r is 1 and $E_4$ is $>CH-O-$, $R_{15}$ is hydrogen or methyl and $R_{16}$ is hydrogen, $C_1$-$C_{18}$alkyl, $C_5$-$C_{12}$cycloalkyl which is unsubstituted or mono-, di- or tri-substituted by $C_1$-$C_4$alkyl, $C_7$-$C_9$phenylalkyl which is unsubstituted or mono-, di- or tri-substituted on the phenyl by $C_1$-$C_4$alkyl, or a group of the formula (III), and, if n is 3, A is aliphatic $C_4$-$C_{18}$triacyl, aliphatic $C_6$-$C_{18}$triacyl containing a trisubstituted nitrogen atom, aromatic $C_9$-$C_{18}$triacyl, heterocyclic triacyl containing up to 18 carbon atoms, or A is a group of the formula (VII)

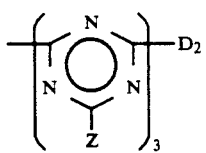 (VII)

in which Z is as defined above and $D_2$ is one of the groups of the formulae (VIIIa)-(VIIId)

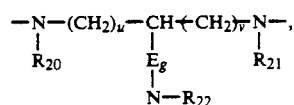 (VIIIa)

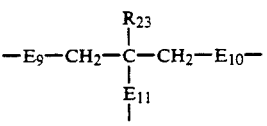 (VIIIb)

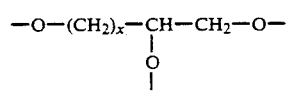 (VIIIc)

$$-O-(CH_2)_x-CH-CH_2-O-$$
$$\phantom{-O-(CH_2)_x-CH}|$$
$$\phantom{-O-(CH_2)_x-CH}O$$
$$\phantom{-O-(CH_2)_x-CH}|$$
(VIIId)

in which $E_5$, $E_6$, $E_7$, $E_9$, $E_{10}$ and $E_{11}$ which can be identical or different are as defined above for $E_1$, $E_2$ and $E_3$ and, if $E_9$ and $E_{10}$ are —O—, $E_{11}$ is also a —$CH_2$—O— group, $R_{17}$, $R_{18}$ and $R_{19}$ which can be identical or different are $C_2$-$C_6$alkylene, t is zero or 1, $R_{20}$, $R_{21}$ and $R_{22}$ which can be identical or different are as defined above for $R_{16}$, $E_8$ is a direct bond or —$CH_2$—, u, v and x which can be identical or different are integers from 2 to 6 and $R_{23}$ is hydrogen or $C_1$-$C_8$alkyl, and, if n is 4, A is aliphatic $C_6$-$C_{18}$tetraacyl, aliphatic $C_{10}$-$C_{18}$tetraacyl containing 2 trisubstituted nitrogen atoms, aromatic $C_{10}$-$C_{18}$tetraacyl, cycloaliphatic $C_{10}$-$C_{22}$tetraacyl or a group of the formula (IX)

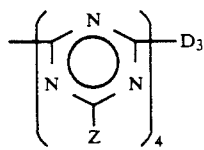 (IX)

in which Z is as defined above and $D_3$ is a group of the formula (Xa) or (Xb)

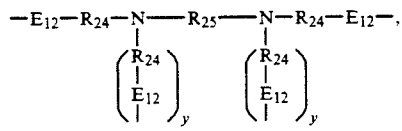 (Xa)

-continued
$$R_{26}-(O-)_4 \quad (Xb)$$

in which $E_{12}$ is as defined above for $E_1$, $E_2$ and $E_3$, $R_{24}$ and $R_{25}$ which can be identical or different are $C_2$-$C_6$alkylene, y is zero or 1 and $R_{26}$ is $C_4$-$C_{12}$alkanetetrayl.

2. A compound of the formula (I) according to claim 1, in which $R_1$ and $R_9$ which can be identical or different are hydrogen, $C_1$-$C_4$alkyl, OH, $C_6$-$C_{12}$alkoxy, $C_5$-$C_8$cycloalkoxy, allyl, benzyl, acetyl or 2-hydroxyethyl.

3. A compound of the formula (I) according to claim 1, in which $R_2$ is $C_2$-$C_6$alkylene, m is zero or 1, n is 1, 2, 3 or 4 and, if n is 1, A is hydrogen, $C_1$-$C_{18}$alkyl, $C_3$-$C_6$alkenyl or benzyl or A is one of the groups of the formulae (IIa)-(IId) in which X and Y which can be identical or different are a group —$OR_6$, —$SR_6$ or

where $R_6$, $R_7$ and $R_8$ which can be identical or different are hydrogen, $C_1$-$C_{18}$alkyl, $C_5$-$C_8$cycloalkyl which is unsubstituted or mono-, di- or tri-substituted by $C_1$-$C_4$alkyl, $C_3$-$C_{18}$alkenyl, phenyl which is unsubstituted or mono-, di- or tri-substituted by $C_1$-$C_4$alkyl or by $C_1$-$C_4$alkoxy, benzyl, $C_2$-$C_3$alkyl substituted in the 2- or 3-position by OH, by $C_1$-$C_4$alkoxy or by di-($C_1$-$C_4$alkyl)-amino, tetrahydrofurfuryl or a group of the formula (III), or the group

is 1-pyrrolidyl, 1-piperidyl, 4-morpholinyl or 1-hexahydroazepinyl, $R_3$ is hydrogen, $C_1$-$C_{17}$alkyl, $C_5$-$C_8$cycloalkyl which is unsubstituted or mono-, di- or tri-substituted by $C_1$-$C_4$alkyl, $C_2$-$C_{17}$alkenyl, phenyl which is unsubstituted or mono-, di- or tri-substituted by $C_1$-$C_4$alkyl and/or by an OH group, $C_7$-$C_8$phenylalkyl which is unsubstituted or mono-, di- or tri-substituted on the phenyl by $C_1$-$C_4$alkyl and/or by an OH group, p is zero or 1, $R_4$ is $C_1$-$C_{18}$alkyl, $C_5$-$C_8$cycloalkyl which is unsubstituted or mono-, di- or tri-substituted by $C_1$-$C_4$alkyl, $C_3$-$C_{18}$alkenyl or a group of the formula (III) and $R_5$ is $C_1$-$C_{12}$alkyl, phenyl or tolyl, and, if n is 2, A is $C_2$-$C_{10}$alkylene, $C_4$-$C_{10}$alkylene interrupted by 1, 2 or 3 oxygen atoms, 2-hydroxytrimethylene, xylylene or one of the groups of the formulae (IVa)-(IVe) in which q is an integer from 1 to 5, $R_{10}$ is a direct bond, $C_1$-$C_{10}$alkylene or cyclohexylene, $R_{11}$ is $C_2$-$C_{10}$alkylene, $C_4$-$C_{10}$alkylene interrupted by 1, 2 or 3 oxygen atoms, cyclohexylenedimethylene, isopropylidenedicyclohexylene or isopropylidenediphenylene, Z is as defined above for X and Y or a group of the formula (V), $D_1$ is one of the groups of the formulae (VIa)-(VIc) in which $E_1$, $E_2$ and $E_3$ which can be identical or different are —O— or

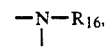

$R_{12}$ is as defined above for $R_{11}$, methylenedicyclohexylene or $C_4$-$C_{12}$alkylene interrupted by 1 or 2 groups

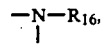

$R_{13}$ is $C_2$-$C_6$alkylene, $E_4$ is

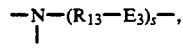

$>CH\text{—}O\text{—}$ or 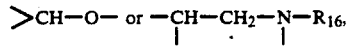

r and s which can be identical or different are zero or 1, $R_{14}$ is hydrogen or also methyl if r is 1 and $E_4$ is $>CH\text{—}O\text{—}$, $R_{15}$ is hydrogen or methyl and $R_{16}$ is hydrogen, $C_1$-$C_{12}$alkyl, $C_5$-$C_8$cycloalkyl which is unsubstituted or mono-, di- or tri-substituted by $C_1$-$C_4$alkyl, benzyl or a group of the formula (III), and, if n is 3, A is aliphatic $C_4$-$C_{12}$triacyl, a group $N\text{—}(CH_2\text{—}CO\text{—})_3$, aromatic or heterocyclic triacyl containing up to 12 carbon atoms or A is a group of the formula (VII) in which Z is as defined above and $D_2$ is one of the groups of the formulae (VIIIa)-(VIIId) in which $E_5$, $E_6$, $E_7$, $E_9$, $E_{10}$ and $E_{11}$ which can be identical or different are as defined above for $E_1$, $E_2$ and $E_3$ and, if $E_9$ and $E_{10}$ are $\text{—}O\text{—}$, $E_{11}$ is also a $\text{—}CH_2\text{—}O\text{—}$ group, $R_{17}$, $R_{18}$ and $R_{19}$ which can be identical or different are $C_2$-$C_6$alkylene, t is zero or 1, $R_{20}$, $R_{21}$ and $R_{22}$ which can be identical or different are as defined above for $R_{16}$, $E_8$ is a direct bond or $\text{—}CH_2\text{—}$, u, v and x which can be identical or different are integers from 2 to 6 and $R_{23}$ is hydrogen or $C_1$-$C_4$alkyl, and, if n is 4, A is aliphatic $C_6$-$C_8$tetraacyl, aliphatic $C_{10}$-$C_{14}$tetraacyl containing two trisubstituted nitrogen atoms or a group of the formula (IX) in which Z is as defined above and $D_3$ is a group of the formula (Xa) or (Xb) in which $E_{12}$ is as defined above for $E_1$, $E_2$ and $E_3$, $R_{24}$ and $R_{25}$ which can be identical or different are $C_2$-$C_6$alkylene, y is zero or 1 and $R_{26}$ is $C_4$-$C_8$alkanetetrayl.

4. A compound of the formula (I) according to claim 1, in which $R_2$ is $C_2$-$C_3$alkylene, m is zero or 1, n is 1, 2, 3 or 4 and, if n is 1, A is hydrogen, $C_1$-$C_{18}$alkyl, allyl, benzyl or A is one of the groups of the formulae (IIa)-(IId) in which X and Y which can be identical or different are a group $\text{—}OR_6$, $\text{—}SR_6$ or

where $R_6$, $R_7$ and $R_8$ which can be identical or different are hydrogen, $C_1$-$C_{12}$alkyl, cyclohexyl which is unsubstituted or mono-, di- or tri-substituted by $C_1$-$C_4$alkyl, allyl, undecenyl, oleyl, phenyl, benzyl, $C_2$-$C_3$alkyl substituted in the 2- or 3-position by OH, by $C_1$-$C_4$alkoxy, by dimethylamino or by diethylamino, tetrahydrofurfuryl or a group of the formula (III), or the group

is 4-morpholinyl, $R_3$ is $C_1$-$C_{17}$alkyl, cyclohexyl which is unsubstituted or mono-, di- or tri-substituted by $C_1$-$C_4$alkyl, $C_2$-$C_{10}$alkenyl, phenyl, t-butylphenyl, 3,5-di-t-butyl-4-hydroxyphenyl, benzyl or 2-(3,5-di-t-butyl-4-hydroxyphenyl)-ethyl, p is zero or 1, $R_4$ is $C_1$-$C_{18}$alkyl, cyclohexyl which is unsubstituted or mono-, di- or trisubstituted by $C_1$-$C_4$alkyl, allyl, undecenyl, oleyl or a group of the formula (III) and $R_5$ is $C_1$-$C_8$alkyl, phenyl or tolyl and, if n is 2, A is $C_2$-$C_8$alkylene, $C_4$-$C_8$alkylene interrupted by 1 or 2 oxygen atoms, 2-hydroxytrimethylene, xylylene or one of the groups of the formulae (IVa)-(IVe) in which q is an integer from 1 to 3, $R_{10}$ is a direct bond or $C_1$-$C_8$alkylene, $R_{11}$ is $C_2$-$C_8$alkylene, $C_4$-$C_8$alkylene interrupted by 1 or 2 oxygen atoms, cyclohexylenedimethylene, isopropylidenedicyclohexylene or isopropylidenediphenylene, Z is as defined above for X and Y or is a group of the formula (V), $D_1$ is one of the groups of the formulae (VIa)-(VIc) in which $E_1$, $E_2$ and $E_3$ which can be identical or different are $\text{—}O\text{—}$ or

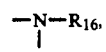

$R_{12}$ is as defined above for $R_{11}$, methylenedicyclohexylene or $C_4$-$C_{10}$alkylene interrupted by 1 or 2 groups

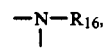

$R_{13}$ is $C_2$-$C_3$alkylene, $E_4$ is

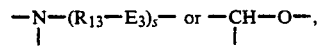

r and s which can be identical or different are zero or 1, $R_{14}$ is hydrogen or also methyl if r is 1 and $E_4$ is $>CH\text{—}O\text{—}$, $R_{15}$ is hydrogen or methyl and $R_{16}$ is hydrogen, $C_1$-$C_8$alkyl, cyclohexyl which is unsubstituted or mono-, di- or tri-substituted by $C_1$-$C_4$alkyl, benzyl or a group of the formula (III), and, if n is 3, A is aliphatic $C_4$-$C_8$triacyl, 1,2,4-benzenetricarbonyl, 1,3,5-benzenetricarbonyl or A is a group of the formula (VII) in which Z is as defined above and $D_2$ is one of the groups of the formulae (VIIIa)-(VIIId) in which $E_5$, $E_6$, $E_7$, $E_9$, $E_{10}$ and $E_{11}$ which can be identical or different are as defined above for $E_1$, $E_2$ and $E_3$ and, if $E_9$ and $E_{10}$ are $\text{—}O\text{—}$, $E_{11}$ is also a group $\text{—}CH_2\text{—}O\text{—}$, $R_{17}$, $R_{18}$ and $R_{19}$ which can be identical or different are $C_2$-$C_6$alkylene, t is zero or 1, $R_{20}$, $R_{21}$ and $R_{22}$ which can be identical or different are as defined above for $R_{16}$, $E_8$ is a direct bond or $\text{—}CH_2\text{—}$, u, v and x which can be identical or different are integers from 2 to 6, $R_{23}$ is hydrogen, methyl or ethyl, and, if n is 4, A is aliphatic $C_6$-$C_8$tetraacyl or a group of the formula (IX) in which Z is as defined above and $D_3$ is a group of the formula (Xa) or (Xb) in which $E_{12}$ is as defined above for $E_1$, $E_2$ and $E_3$, $R_{24}$ and $R_{25}$ which can be identical or different are $C_2$-$C_6$alkylene, y is zero or 1 and $R_{26}$ is $C_4$-$C_6$alkanetetrayl.

5. A compound of the formula (I) according to claim 1, in which $R_2$ is $C_2$-$C_3$alkylene, m is zero or 1, n is 1, 2, 3 or 4 and, if n is 1, A is hydrogen, methyl, $C_4$-$C_{18}$alkyl or A is one of the groups of the formulae (IIa)-(IIc) in which X and Y which can be identical or different are a group $\text{—}OR_6$ or

where $R_6$ is $C_1$–$C_8$alkyl, 2,2,6,6-tetramethyl-4-piperidyl or 1,2,2,6,6-pentamethyl-4-piperidyl, $R_7$ and $R_8$ which can be identical or different are $C_1$–$C_{12}$alkyl, cyclohexyl, benzyl, $C_2$–$C_3$alkyl substituted in the 2- or 3-position by methoxy, by ethoxy, by dimethylamino or by diethylamino, tetrahydrofurfuryl, 2,2,6,6-tetramethyl-4-piperidyl or 1,2,2,6,6-pentamethyl-4-piperidyl or $R_7$ is also hydrogen or the group

is 4-morpholinyl, $R_3$ is $C_3$–$C_{17}$alkyl, cyclohexyl, phenyl, 3,5-di-t-butyl-4-hydroxyphenyl or 2-(3,5-di-t-butyl-4-hydroxyphenyl)-ethyl, p is zero, $R_4$ is $C_2$–$C_{18}$alkyl, cyclohexyl, trimethylcyclohexyl, t-butylcyclohexyl, 2,2,6,6-tetramethyl-4-piperidyl or 1,2,2,6,6-pentamethyl-4-piperidyl and, if n is 2, A is one of the groups of the formulae (IVa)–(IVe) in which q is 1, $R_{10}$ is a direct bond or $C_1$–$C_8$alkylene, $R_{11}$ is $C_2$–$C_8$alkylene, cyclohexylenedimethylene or isopropylidenedicyclohexylene, Z is as defined above for X and Y or is a group of the formula (V), $D_1$ is one of the groups of the formulae (VIa)–(VIc) in which $E_1$ and $E_2$ which can be identical or different are —O— or

$R_{12}$ is $C_2$–$C_8$alkylene, cyclohexylenedimethylene or methylenedicyclohexylene, the group (VIb) is

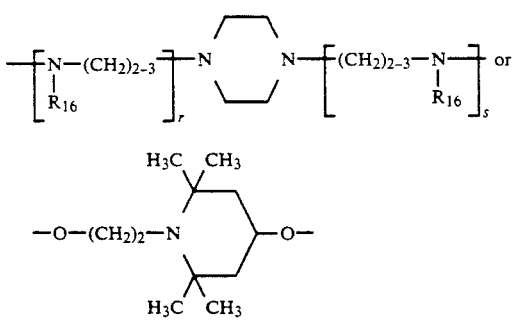

where r and s which can be identical or different are zero or 1, $R_{16}$ is hydrogen, $C_1$–$C_4$alkyl, cyclohexyl, 2,2,6,6-tetramethyl-4-piperidyl or 1,2,2,6,6-pentamethyl-4-piperidyl and $R_{15}$ is hydrogen or methyl, and, if n is 3, A is a group of the formula (VII) in which Z is as defined above and $D_2$ is a group of the formula (VIIIa) or (VIIIb) in which $E_5$, $E_6$ and $E_7$ which can be identical or different are as defined above for $E_1$ and $E_2$, $R_{17}$ and $R_{18}$ which can be identical or different are $C_2$–$C_6$alkylene, t is zero, $R_{20}$, $R_{21}$ and $R_{22}$ are as defined above for $R_{16}$, $E_8$ is a direct bond or —$CH_2$— and u and v which can be identical or different are integers from 2 to 6, and, if n is 4, A is a group of the formula (IX) in which Z is as defined above and $D_3$ is a group of the formula (Xa) in which $E_{12}$ is as defined above for $E_1$ and $E_2$, $R_{24}$ and $R_{25}$ which can be identical or different are $C_2$–$C_3$alkylene and y is zero.

6. A compound of the formula (I) according to claim 1, in which $R_1$ is hydrogen or methyl, $R_2$ is ethylene, m is zero or 1, n is 1, 2, 3 or 4 and, if n is 1, A is hydrogen, methyl, $C_8$–$C_{18}$alkyl or A is one of the groups of the formulae (IIa)–(IIc) in which X and Y which can be identical or different are a group —$OR_6$ or

where $R_6$ is $C_1$–$C_4$alkyl, 2,2,6,6-tetramethyl-4-piperidyl or 1,2,2,6,6-pentamethyl-4-piperidyl, $R_7$ and $R_8$ which can be identical or different are $C_1$–$C_8$alkyl, cyclohexyl, tetrahydrofurfuryl, 2,2,6,6-tetramethyl-4-piperidyl or 1,2,2,6,6-pentamethyl-4-piperidyl, or $R_7$ is also hydrogen, or the group

is 4-morpholinyl, $R_3$ is $C_4$–$C_{17}$alkyl, p is zero and $R_4$ is $C_2$–$C_{18}$alkyl, cyclohexyl, t-butylcyclohexyl, 2,2,6,6-tetramethyl-4-piperidyl or 1,2,2,6,6-pentamethyl-4-piperidyl, and, if n is 2, A is one of the groups of the formulae (IVb)–(IVe) in which $R_{10}$ is $C_2$–$C_8$alkylene, $R_{11}$ is $C_4$–$C_6$alkylene, Z is as defined above for X and Y or a group of the formula (V), $D_1$ is 1,4-piperazinediyl or a group of the formula (VIa) in which $E_1$ and $E_2$ are

$R_{12}$ is $C_2$–$C_6$alkylene or methylenedicyclohexylene, $R_{16}$ is hydrogen, methyl, 2,2,6,6-tetramethyl-4-piperidyl or 1,2,2,6,6-pentamethyl-4-piperidyl, and, if n is 3, A is a group of the formula (VII) in which Z is as defined above and $D_2$ is a group

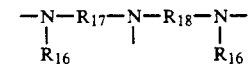

in which $R_{16}$ is as defined above and $R_{17}$ and $R_{18}$ are $C_2$–$C_3$alkylene, and, if n is 4, A is a group of the formula (IX) in which Z is as defined above and $D_3$ is a group

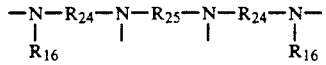

in which $R_{16}$ is as defined above and $R_{24}$ and $R_{25}$ which can be identical or different are $C_2$–$C_3$alkylene.

7. A compound of the formula (I) according to claim 1, in which $R_1$ is hydrogen or methyl, $R_2$ is ethylene, m is zero or 1, n is 1, 2 or 3 and, if n is 1, A is hydrogen, methyl, $C_8$–$C_{18}$alkyl or A is one of the groups of the formulae (IIa)–(IIc) in which X and Y which can be identical or different are

where $R_7$ and $R_8$ which can be identical or different are $C_1$–$C_8$alkyl, 2,2,6,6-tetramethyl-4-piperidyl or 1,2,2,6,6-pentamethyl-4-piperidyl, or $R_7$ is also hydrogen, or the group

is 4-morpholinyl, $R_3$ is $C_4$–$C_{17}$alkyl, p is zero and $R_4$ is $C_2$–$C_{18}$alkyl, and, if n is 2, A is one of the groups of the formulae (IVb)–(IVe) in which $R_{10}$ is $C_2$–$C_8$alkylene, $R_{11}$ is $C_4$–$C_6$alkylene, Z is as defined above for X and Y or a group of the formula (V), $D_1$ is 1,4-piperazindiyl or a group of the formula (VIa) in which $E_1$ and $E_2$ are

$R_{12}$ is $C_2$–$C_6$alkylene, $R_{16}$ is 2,2,6,6-tetramethyl-4-piperidyl or 1,2,2,6,6-pentamethyl-4-piperidyl, and, if n is 3, A is a group of the formula (VII) in which Z is as defined above and $D_2$ is a group

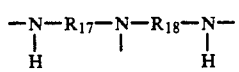

in which $R_{17}$ and $R_{18}$ are $C_2$–$C_3$alkylene.

8. A compound of the formula

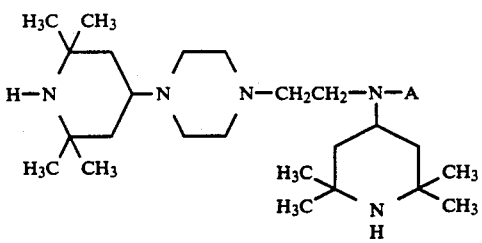

wherein A is 2,2-dimethyl-1-propanoyl, n-butoxycarbonyl, n-tetradecyloxycarbonyl or 2,4-bis[N-butyl-(2',2',6',6'-pentamethyl-4'-piperidyl)amino]triazin-6-yl, and the compound of the formula

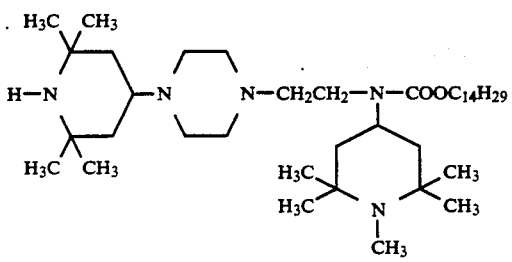

according to claim 1.

* * * * *